United States Patent
Spivey et al.

(10) Patent No.: US 9,538,999 B2
(45) Date of Patent: Jan. 10, 2017

(54) SUTURE STORAGE DEVICES, SYSTEMS, AND METHODS

(71) Applicant: Medos International Sàrl, Le Locle (CH)

(72) Inventors: James T. Spivey, Whitehouse Station, NJ (US); Kevin J. Zylka, Raynham, MA (US); Justin Piccirillo, Uxbridge, MA (US); Brian Otrando, Cumberland, RI (US); Douglas Hester, Dartmouth, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 596 days.

(21) Appl. No.: 13/800,566

(22) Filed: Mar. 13, 2013

(65) Prior Publication Data

US 2014/0277125 A1 Sep. 18, 2014

(51) Int. Cl.
*A61B 17/04* (2006.01)
*A61B 17/06* (2006.01)
*A61B 17/00* (2006.01)

(52) U.S. Cl.
CPC ....... *A61B 17/0401* (2013.01); *A61B 17/0483* (2013.01); *A61B 17/06133* (2013.01);
(Continued)

(58) Field of Classification Search
CPC .......... A61B 17/06133; A61B 17/061061; A61B 17/06114; A61B 17/06138; A61B 2017/06142; A61B 2017/06152; A61B 2017/06157; A61B 17/06119; A61B 17/06123; A61B 17/06128; A61B 2017/06147; A61B 2017/0416; D05B 91/0012; D05B 91/14; D05B 91/16; D05B 97/10; A41H 3/01; A41H 3/015; A41H 31/00; A41H 17/00; A41H 19/00; A45D 8/185; B65D 85/04; B65D 85/08; B65D 85/24; B65D 85/675; B65D 85/67
(Continued)

(56) References Cited

U.S. PATENT DOCUMENTS 4,244,370 A 1/1981 Furlow et al.
4,341,206 A 7/1982 Perrett et al.
(Continued)

FOREIGN PATENT DOCUMENTS

FR 1456856 A 7/1966

OTHER PUBLICATIONS

Extended European Search Report for Application No. 14159164.4 issued Sep. 17, 2014 (8 pages).

*Primary Examiner* — Jonathan Miles
*Assistant Examiner* — Kendra Obu

(57) ABSTRACT

Devices, systems, and methods are provided for managing suture filaments when performing soft tissue repair. One exemplary embodiment of a surgical suture management device is in the form of a suture loop management card. The card can generally be configured to hold open a collapsible loop of suture until a force applied to the loop is greater than a threshold tension. The card can include a number of different features that help to keep the loop open until the threshold tension is achieved, including features designed to prevent the filament from being mistakenly offloaded. The card can be configured to be removably inserted into a handle of an inserter tool for use as a surgical tissue repair system. Other devices, systems, and methods for performing soft tissue repair are also provided.

14 Claims, 21 Drawing Sheets

(52) U.S. Cl.
CPC ......... *A61B 17/06* (2013.01); *A61B 17/06114* (2013.01); *A61B 17/06119* (2013.01); *A61B 17/06123* (2013.01); *A61B 17/06128* (2013.01); *A61B 17/06138* (2013.01); *A61B 2017/0053* (2013.01); *A61B 2017/0409* (2013.01); *A61B 2017/0412* (2013.01); *A61B 2017/0416* (2013.01); *A61B 2017/0427* (2013.01); *A61B 2017/0496* (2013.01); *A61B 2017/06142* (2013.01); *A61B 2017/06147* (2013.01); *A61B 2017/06152* (2013.01)

(58) Field of Classification Search
USPC ........................................................ 606/228
See application file for complete search history.

(56) References Cited

U.S. PATENT DOCUMENTS

| | | | |
|---|---|---|---|
| 4,710,075 A | | 12/1987 | Davison |
| 5,029,573 A | | 7/1991 | Chow |
| 5,078,730 A | | 1/1992 | Li et al. |
| 5,092,455 A | * | 3/1992 | Leary ........................ 206/63.3 |
| 5,123,528 A | * | 6/1992 | Brown ............. A61B 17/06138 206/63.3 |
| 5,127,518 A | * | 7/1992 | Holzwarth ....... A61B 17/06138 206/63.3 |
| 5,131,534 A | * | 7/1992 | Brown ............. A61B 17/06123 206/339 |
| 5,174,087 A | * | 12/1992 | Bruno ................ A61B 17/0401 206/63.3 |
| 5,269,796 A | | 12/1993 | Miller et al. |
| 5,279,553 A | | 1/1994 | Winkler et al. |
| 5,354,298 A | | 10/1994 | Lee et al. |
| 5,478,345 A | | 12/1995 | Stone et al. |
| 5,487,469 A | * | 1/1996 | Roshdy ............ A61B 17/06138 206/363 |
| 5,529,175 A | * | 6/1996 | Brunken .......... A61B 17/06138 206/63.3 |
| 5,578,057 A | | 11/1996 | Wenstrom, Jr. |
| 5,669,490 A | * | 9/1997 | Colligan et al. ............. 206/63.3 |
| 5,715,942 A | * | 2/1998 | Li ......................... A61B 17/04 206/339 |
| 5,752,963 A | | 5/1998 | Allard et al. |
| 5,755,729 A | | 5/1998 | de la Torre et al. |
| 5,788,062 A | * | 8/1998 | Cerwin et al. ............... 206/63.3 |
| 5,814,051 A | | 9/1998 | Wenstrom, Jr. |
| 5,843,087 A | | 12/1998 | Jensen et al. |
| 5,846,181 A | | 12/1998 | Heckele et al. |
| 5,948,002 A | | 9/1999 | Bonutti |
| 6,080,184 A | | 6/2000 | Peters et al. |
| 6,146,407 A | | 11/2000 | Krebs |
| 6,241,736 B1 | | 6/2001 | Sater et al. |
| 6,260,696 B1 | * | 7/2001 | Braginsky et al. .......... 206/63.3 |
| 7,329,264 B2 | | 2/2008 | Merves |
| 7,645,293 B2 | | 1/2010 | Martinek et al. |
| 8,307,978 B2 | | 11/2012 | Kirsch et al. |
| 2003/0204193 A1 | | 10/2003 | Gabriel et al. |
| 2004/0106935 A1 | | 6/2004 | Merves |
| 2008/0119874 A1 | | 5/2008 | Merves |
| 2009/0171143 A1 | | 7/2009 | Chu et al. |
| 2009/0306711 A1 | * | 12/2009 | Stone et al. ................... 606/232 |
| 2010/0249809 A1 | | 9/2010 | Singhatat et al. |
| 2010/0305576 A1 | | 12/2010 | Ferguson et al. |

\* cited by examiner

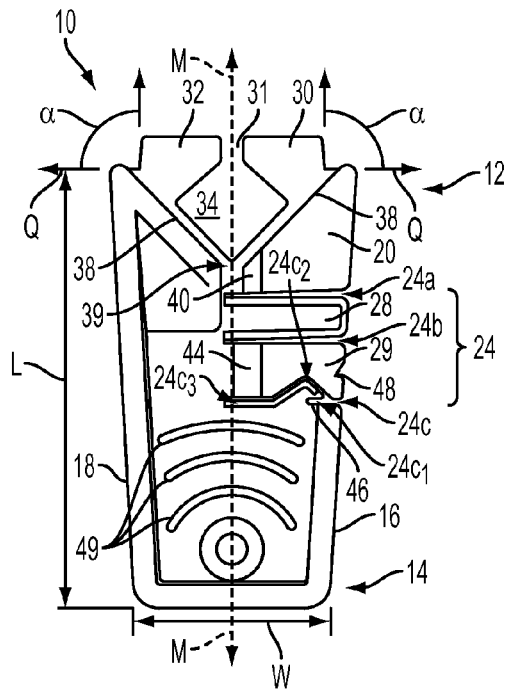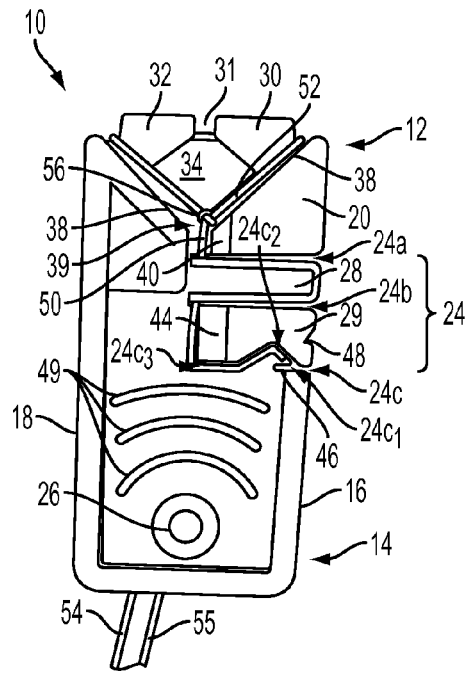
FIG. 3A    FIG. 3B
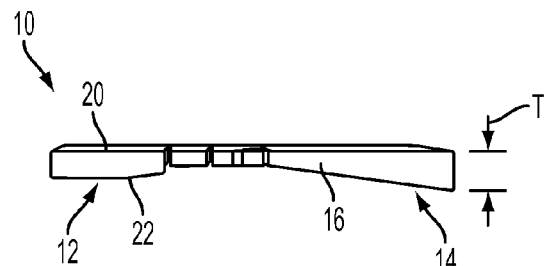
FIG. 3C
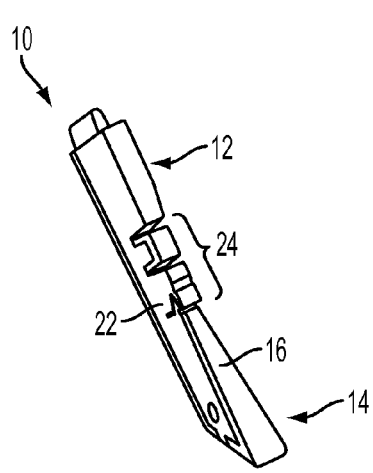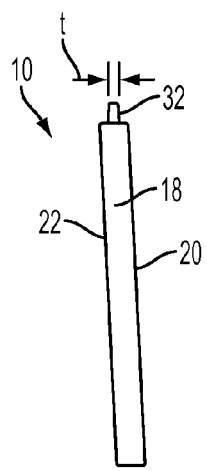
FIG. 3D    FIG. 3E

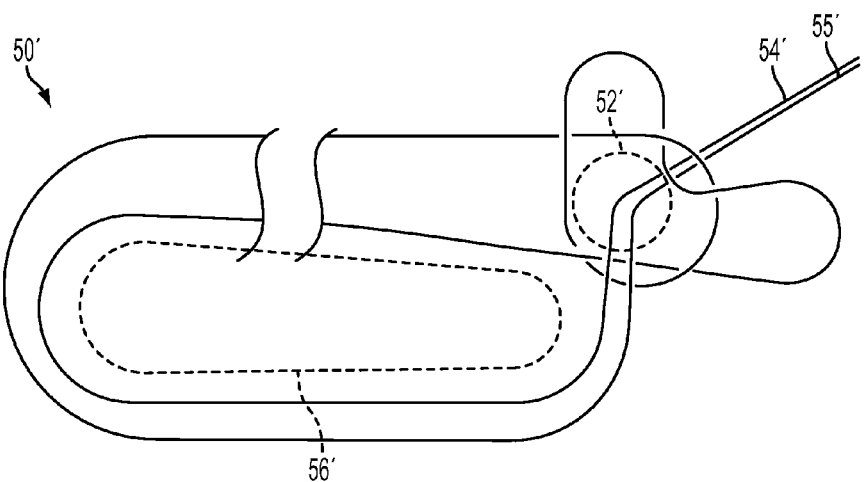
FIG. 7A
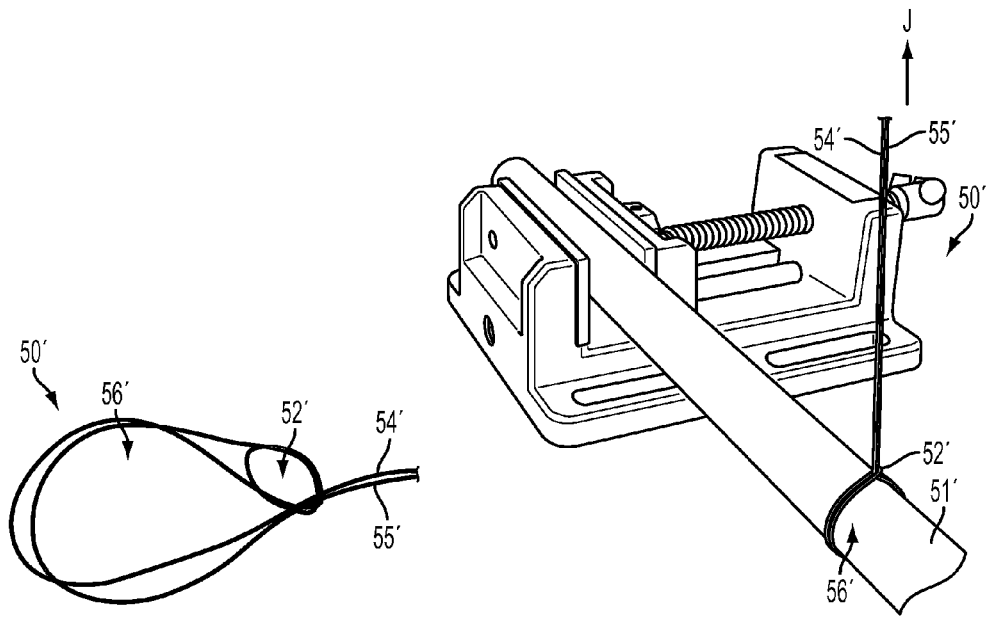
FIG. 7B
FIG. 7C

SUTURE STORAGE DEVICES, SYSTEMS, AND METHODS

FIELD

The present disclosure relates to devices, systems, and methods for securing soft tissue to bone, and more particularly relates to managing suture filament used to secure the tissue to bone.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks, at least some of which are used in conjunction with suture to perform repair procedures.

Devices that use suture to help secure tissue to bone often present difficulties in suture management during the repair procedure. Even when just a single suture filament is used as part of a repair system, that filament typically has multiple limbs that must be accounted for during the repair. For example, in some embodiments a filament includes two limbs that extend from one side of a suture anchor and two other limbs that extend from the other side of the suture anchor. When a surgeon is utilizing an inserter tool to implant the anchor, the four terminal ends can be in the surgeon's way. However, once the anchor is implanted, surgeons generally want to be able to easily access the terminal ends that were previously in their way so they can use the suture to secure the tissue to bone.

Features currently used to assist in suture management by placing terminal ends out of the way during anchor implantation often require the surgeon to perform multiple steps to subsequently access the terminal ends after the anchor is implanted. For example, an inserter tool may have suture terminal ends extending from one side of the anchor stored in a first location and suture terminal ends extending from the other side of the anchor stored in a second location a distance apart from the first location. In order to access all of the terminal ends for use in securing tissue to bone, the surgeon must perform one action to access the terminal ends stored at the first location and another action to access the terminal ends stored at the second location. These actions are further complicated by the need to hold the accessed set of terminal ends while performing the second action to access the second set of terminal ends.

Additionally, devices currently used to manage sutures can be difficult to use, which can lead to misuse by the operator. Misuse of a suture management device can defeat its intended purpose. For example, if a suture management device is configured to hold open a loop of a particular portion of suture until terminal ends are passed through, but the surgeon mistakenly collapses the loop before passing the terminal ends through the loop, such failure can result in a suture that is no longer useful to the surgeon. The surgeon may then have to remove the anchor and suture and begin the implantation portion of the procedure again.

Accordingly, it is desirable to provide devices, systems, and methods that make it easy for surgeons to manage suture when implanting anchors, but also easy to access and use the suture after the anchor is implanted. It is also desirable to reduce the number of steps to be performed by the surgeon to implant the anchor, access the suture after the anchor is implanted, and subsequently use the suture to attach tissue to bone. Further, it is desirable to incorporate mechanisms into devices and systems used in soft tissue repair that reduce the likelihood of operator errors.

SUMMARY

Devices, systems, and methods are generally provided for managing surgical suture filaments during soft tissue repair. In one exemplary embodiment, a surgical suture management device includes a suture loop management card configured to hold open a collapsible loop of suture. The suture management card can include first and second ends that define a length of the card, first and second sidewalls extending between the first and second ends that define a width of the card, and first and second surfaces that define a thickness of the card. In some embodiments, the suture management card can be substantially rectangular in shape. A plurality of adjacent slots can be formed in the card and disposed between the first and second ends. Each slot can extend from the first sidewall and toward the second sidewall, and can be configured to receive a portion of one or more limbs of the suture that also form the collapsible loop.

The card can have a number of useful features associated therewith. For example, an opening can be formed in the second end of the body and can be configured to receive a distal portion of one or more limbs of the suture. The first end of the card can include first and second prongs that are configured to hold open the collapsible loop of suture until a force applied to the loop is greater than a threshold tension. In some embodiments, the first end can include an opposed pair of seating grooves formed in the first surface of the card. Each seating groove can extend diagonally from the first end and toward the second end, with the seating grooves meeting at a vertex substantially centered between the first and second sidewalls and in communication with a longitudinal seating groove formed in the first surface of the card. The seating grooves can be configured to receive a length of the collapsible loop therein and the longitudinal seating groove can be configured to receive a sliding knot of the collapsible loop.

The plurality of slots can include a first slot and a second slot, with the first and second slots being substantially parallel to one another and substantially perpendicular to a longitudinal axis extending the length of the card. The first and second slots can terminate at a location that is substantially centered between the first and second sidewalls, with the second slot being disposed closer to the second end than is the first slot. In some embodiments, a third slot can also be included. The third slot can be disposed closer to the second end than is the second slot, and can be defined by three separate portions that are in communication with each other to form the slot. A first portion of the slot can extend from the first sidewall; a second portion of the slot, which is adjacent to and in communication with the first portion, can be substantially V-shaped with a vertex facing the first end; and a third portion of the slot, which is adjacent to and in communication with the second portion, can be substantially parallel to the first and second slots.

Additional features can be formed in the card that can assist in preventing premature and mistaken detachment of the suture from the card. One such feature can be a catch slot formed in the body. The catch slot can extend from the first portion of the third slot, toward the second sidewall, and inward of a base of the V-shaped second portion. Another such feature can be a notch formed in the first sidewall, the notch being disposed between the second and third slots. A third such feature can be a raised surface formed on the first surface of the body between the second and the third slots.

Features to assist in placing the card in a handle of an insertion tool can also be included on the card. For example, a protrusion can be formed on the second surface of the body. The protrusion can be configured to engage a complementary retention feature of an insertion tool to secure the device in the tool.

In some embodiments the card can be pre-loaded with a suture. The suture can have a sliding knot formed therein. On one side of the sliding knot can be a collapsible loop, while on the other side of the sliding knot can be first and second free limbs. The collapsible loop can be held open by the first end of the suture management card, and the first and second free limbs can be disposed in the plurality of adjacent slots formed in the body of the card.

One exemplary embodiment of a surgical implant system includes an implant inserter device, a suture having a collapsible loop defined by a sliding knot and first and second free limbs extending on a side of the sliding knot opposite the collapsible loop, and a suture management card configured to hold open the collapsible loop until a force applied to the loop is greater than a threshold tension. The inserter device can have a handle and a shaft extending distally from the handle, with a slot formed in the handle. The slot can be configured to receive the suture management card, while the distal end of the shaft can be configured to engage a surgical implant. The suture management card can be configured to be selectively inserted in and removed from the handle slot. The card can also be configured such that when it is removed from the handle slot, the first and second free limbs of the suture are accessible and capable of being disposed through an opening of the collapsible loop held open by the card so that the free limbs can be used to apply a force to the loop.

In some embodiments, the suture management card can include a first end configured to hold open the collapsible loop until a force applied to the loop is greater than the threshold tension, a second end having an opening formed therein and configured to receive a distal portion of the first and second free limbs, and first and second sidewalls extending between the first and second ends. The opening formed in the second end can extend from the second sidewall and toward the first sidewall, terminating prior to the first sidewall. Other configurations of the opening are also possible.

The handle can include first and second suture-receiving slots formed in a distal end thereof. Each slot can be configured to receive the first and second free limbs that extend distally from the sliding knot on the side opposite of the collapsible loop. The second suture-receiving slot can further include a pinch point formed in a portion thereof. The pinch point can be configured to engage the first and second free limbs from opposed sides when the suture management card is disposed in the handle. Further, the pinch point can be configured to release the first and second free limbs when the suture management card is removed from the slot formed in the handle.

The system can also include a surgical implant. The implant can have proximal and distal ends, with the proximal end having a bore formed therein and the distal end having a filament engagement feature configured to receive the first and second free limbs. The proximal end can be coupled to the distal end of the shaft of the inserter tool via the bore. In some embodiments, the first and second free limbs of the filament can be disposed through the implant's bore at the proximal end, around the implant's filament engagement feature at its distal end, and back through the implant's bore before exiting out of the bore at the proximal end.

One exemplary embodiment of a surgical method includes implanting an anchor having a suture coupled thereto at a surgical site using an insertion tool. The insertion tool can have a suture management card removably disposed in a portion thereof, and a collapsible loop of the suture can be held open by the card. A sliding knot formed in the suture can define the collapsible loop. The method can further include removing the suture management card from the handle and grasping a free limb(s) of the suture that is disposed on a side of the sliding knot opposite the collapsible loop. Depending on the configuration of the card, the free limb(s) may fall away from the card as the card is removed, while in other embodiments the surgeon can disassociate the free limb(s) from the card. The surgeon can then position a distal end of the free limb(s) in an opening of the collapsible loop that is maintained by the suture management card. For example, the free limb(s) can be folded over around the collapsible loop, and a force can subsequently be applied to the free limb(s). The force can be sufficient to disengage the collapsible loop from the suture management card. Subsequently, the free limb(s) can be decoupled from the suture management card, after which tension can be applied to the free limb(s) to collapse the sliding knot. The application of tension can also be suitable to advance the knot toward the surgical site to secure tissue to bone, for instance after the knot is fully collapsed.

In some embodiments, the method can include inserting the suture management card into the insertion tool to secure a distal portion of the free limb(s) in the insertion tool during implantation of the suture anchor. In some other embodiments, the step of decoupling the free limb(s) from the suture management card can include applying tension to the free limb(s) in a direction approximately perpendicular to a sidewall of the suture management card. Doing so can free the free limb(s) from one or more resistance features of the suture management card.

In another exemplary embodiment of a surgical method, the method can include inserting a suture to a surgical location using an insertion device. During insertion, the suture can be coupled to a suture management card that is removably and replaceably disposed in the insertion device. The suture can have a looped end extending from one side of a knot that defines the loop attached to the card and a distal portion that extends from the other side of the knot. When the card is removed from the insertion device, both the looped end and the distal portion of the suture can also be removed from the insertion device. The suture can subsequently be removed from the card and used to complete the surgical procedure, for instance by using the suture to hold a tissue at a desired location with respect to bone. In some embodiments, prior to removing the suture from the card, distal ends of the distal portion can be passed through the looped portion, and a force can be applied to the distal portion to eject the looped portion from the card. The looped portion can be collapsed and drawn toward bone to secure a location of tissue with respect to bone.

BRIEF DESCRIPTION OF DRAWINGS

This invention will be more fully understood from the following detailed description taken in conjunction with the accompanying drawings, in which:

FIG. 3A is a top perspective view of a first surface of the first suture management card of FIG. 1;

FIG. 3B is a top perspective view of the first surface of FIG. 3A having a suture attached to the suture management card;

FIG. 3C is a side perspective view of a first sidewall of the first suture management card of FIG. 3A;

FIG. 3D is another side perspective view of the first sidewall of FIG. 3C;

FIG. 3E is a side perspective view of a second sidewall of the suture management card of FIG. 3A;

FIG. 7A is a schematic view of one exemplary embodiment for forming a sliding knot in a suture;

FIG. 7B is a top perspective view of the suture and sliding knot of FIG. 7A;

FIG. 7C is a perspective view of one exemplary embodiment of collapsing the sliding knot of FIG. 7B;

DETAILED DESCRIPTION

Figure 1:
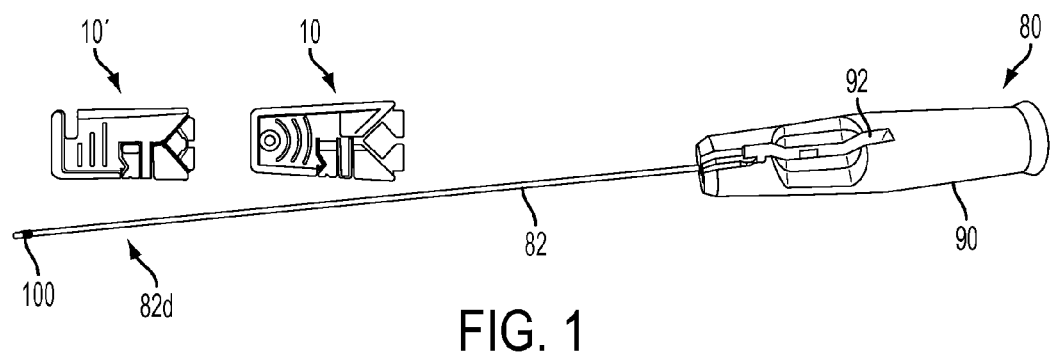
FIG. 1 is a perspective top view of one exemplary embodiment of a system for soft tissue repair, including an inserter tool and two different exemplary embodiments of a suture management card, the first suture management card being located to the right of the second suture management card.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. By way of non-limiting example, features described with respect to one suture management card can generally be applied to the other card configurations provided for herein. Further, in the present disclosure, like-numbered components of the embodiments generally have similar features. Still further, sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Further, to the extent arrows are used to describe a direction a component can be tensioned or pulled, these arrows are illustrative and in no way limit the direction the respective component can be tensioned or pulled. A person skilled in the art will recognize other ways and directions for creating the desired tension or movement. Likewise, while in some embodiments movement of one component is described with respect to another, a person skilled in the art will recognize that other movements are possible. By way of non-limiting example, in embodiments in which a sliding knot is used to help define a collapsible loop, a person skilled in the art will recognize that different knot configurations can change whether moving the knot in one direction will cause a size of an opening defined by the loop to increase or decrease. Additionally, a number of terms may be used throughout the disclosure interchangeably but will be understood by a person skilled in the art. By way of non-limiting example, the terms "suture" and "filament" may be used interchangeably.

The present disclosure generally relates to a surgical suture management device used to assist surgeons in managing suture filaments during a soft tissue repair procedure. The filament, which is typically attached to an anchor implanted in bone, can have multiple limbs that the surgeon must manage during anchor implantation. The surgeon then uses the limbs to draw soft tissue coupled thereto toward the bone in which the anchor is implanted and subsequently secure the tissue at a location proximate to the bone. The management device can be removably included in a handle of an anchor insertion tool, and can include a number of features to assist a surgeon with suture filament management throughout the surgical procedure.

Two exemplary embodiments of suture management devices are illustrated in FIG. 1 as a first suture management card 10 and a second suture management card 10'. The cards 10, 10' can be adapted to fit into a complementary slot 92 formed in a handle 90 of an inserter tool 80. When either of the suture management cards 10, 10' is disposed in the handle 90, limbs of a suture filament attached thereto can extend distally along a shaft 82 of the inserter tool 80, be coupled to an anchor 100 coupled to a distal end 82d of the shaft 82, extend proximally back up the shaft 82, and be coupled to the handle 90.

Figure 2:
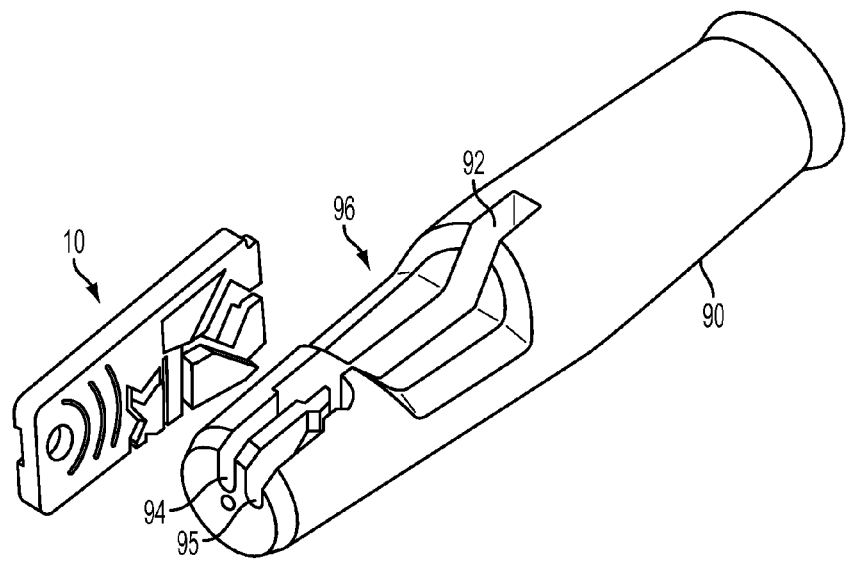
FIG. 2 is a perspective view of a handle of the inserter tool and the first suture management card of FIG. 1.

FIG. 2 illustrates one exemplary embodiment of the handle 90 of inserter tool 80. The handle 90 is adapted to receive one of the suture management cards 10, 10' (such as card 10 shown in FIG. 2) in its slot 92. Further, the handle 90 can include two suture-receiving slots 94, 95 for receiving limbs of suture extending proximally from an anchor, as described in further detail below. Additionally, a cut-out portion 96 can be formed in a portion of the handle 90 to assist with insertion and removal of the card 10. The cut-out portion 96 allows a portion of the inserted card 10 to be exposed, which in turn makes it easier for a surgeon to grasp the card 10 to remove it from the handle 90. After the anchor is inserted into bone, the suture management card 10 can be removed from the handle 90, the suture can be disassociated from the card 10, and the suture can be used to draw tissue to the bone in which the anchor is inserted using techniques known to those skilled in the art.

Figure 3F:
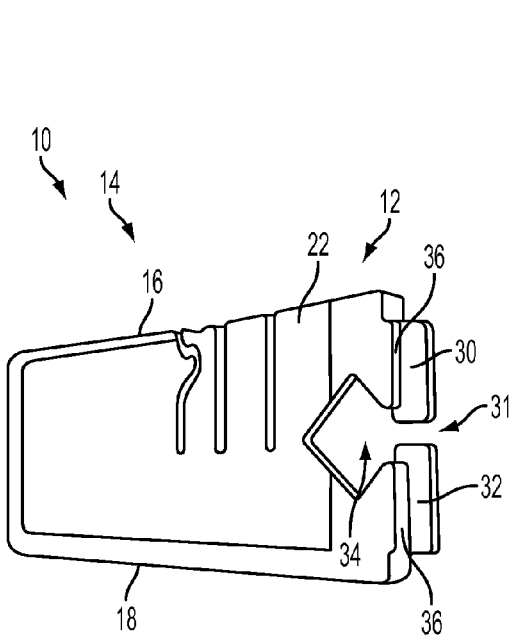
FIG. 3F is a top perspective view of a first end and a second surface of the suture management card of FIG. 3A.

FIGS. 3A-3L illustrate the first exemplary embodiment of a suture management card 10. The card 10 can generally have a substantially polygonal shape (e.g., a rectangular shape) with a proximal or first end 12 and a distal or second end 14 that define a length L of the card 10 (FIG. 3A), a first sidewall 16 and a second sidewall 18 extending between the first and second ends 12, 14 that define a width W of the card 10 (FIG. 3A), and a first surface 20 and a second surface 22 (FIG. 3D) that define a thickness T of the card 10 (FIG. 3C). As shown in FIGS. 3A and 3B, the card 10 can be trapezoidal in shape, with the width W gradually increasing from the second end 14 to the first end 12. In the illustrated embodiment, the gradual increase of the width W coincides with a gradual increase in the diameter of the inserter tool handle 90 in which the card 10 is disposed so that the card 10 can sit approximately flush within the handle 90 along a substantial length of the card 10. As shown in FIGS. 3C and 3D, the card 10 can also have different thicknesses T at various locations between the first and second ends 12, 14. In the illustrated embodiment, the thickness T at a terminal end of the first sidewall 16 at the first end 12 and at a terminal end of the first sidewall 16 at the second end 14 is substantially similar, with the thickness T decreasing between the terminal ends and a central portion of the sidewall 16. As shown in FIG. 3E, a thickness T of the second sidewall 18, on the other hand, can remain substantially the same along its length.

A size and shape of the suture management card 10, as well as the materials from which it is made, can depend, at least in part, on the sizes, shapes, and materials with which it will be used, including the suture filament and inserter tool, and the type of procedure with which it will be used. Accordingly, to the extent the present disclosure describes the card 10 as being polygonal, such as substantially rectangular or trapezoidal, other shapes can also be used without departing from the spirit of the disclosure. In some exemplary embodiments of the card, a length L can be in the range of about 3 centimeters to about 8 centimeters, a width W can be in the range of about 1 centimeter to about 4 centimeters, and a thickness T can be in the range of about 0.5 millimeters to about 6 millimeters. In one exemplary embodiment the card has a length L of about 4.5 centimeters, a width W at the second end of about 2.0 centimeters, a width W at the first end of about 2.5 centimeters, a thickness T at the terminal ends of the first and second sidewalls 16, 18 of about 3.0 millimeters, and a thickness T at central portions of the first and second sidewalls 16, 18 of about 1.0 millimeters and about 3.0 millimeters, respectively. Any number of materials can be used to form the card, including polymers and metals, but in one exemplary embodiment the card is made of polycarbonate.

The first end 12 can be configured to hold open a collapsible loop 52 of suture filament 50, as shown in FIG. 3B. The loop 52 can be defined by a knot 56 formed in the suture filament 50, and one or more limbs 54, 55 can extend distally from the knot 56. The second end 14 can include an opening 26 configured to receive a distal portion of the filament limbs 54, 55, as shown in FIGS. 3J and 3K. As described herein, the filament 50 extends from the card 10, to an anchor, and back to the card 10, with the distal portion being a portion of the limbs 54, 55 extending proximally toward the card 10 from an anchor. A plurality of adjacent slots 24 can be formed in the card 10, between the first and second ends 12, 14, to receive a portion of the limbs 54, 55 that extend distally from the knot 56, as shown in FIGS. 3B, 3I, 3J, and 3K.

Turning to more particular features of the suture management card 10, the first end 12 can include first and second prongs 30, 32, which are shown at least in FIGS. 3A and 3B. The prongs 30, 32 can be configured to hold open the collapsible loop 52 of suture 50 until a force applied to the loop 52 is greater than an ejection threshold tension created by the prongs 30, 32 and adjacent slots 24. It can be useful to maintain an opening of the loop 52 during shipping, and also during a surgical procedure at least until the loop 52 is collapsed. The prongs 30, 32 can have a variety of shapes, but in the illustrated embodiment they extend from the first end 12, a distance beyond the length L, and are polygonal in shape. In some embodiments the prongs 30, 32 can be angled with respect to an axis Q extending along the width W of the card 10. An angle α (FIG. 3A) formed by the prongs 30, 32 with respect the axis Q can be in the range of about 90 degrees to about 110 degrees, and in the illustrated embodiment the angle α is approximately 97 degrees. The prongs 30, 32, along with a portion of the first end 12, define an opening 34 for receiving a distal portion of the suture limbs 54, 55. The distal portions can be passed into the opening 34, and wrapped around the loop 52, to subsequently apply a tension that exceeds the ejection threshold tension, thereby ejecting the loop 52 off the card 10, as described in further detail below. A space 31 located between the prongs 30, 32, and in communication with the opening 34, allows the distal portions to pass therethrough to move away from the card when ejecting the loop 52.

Figure 3G:
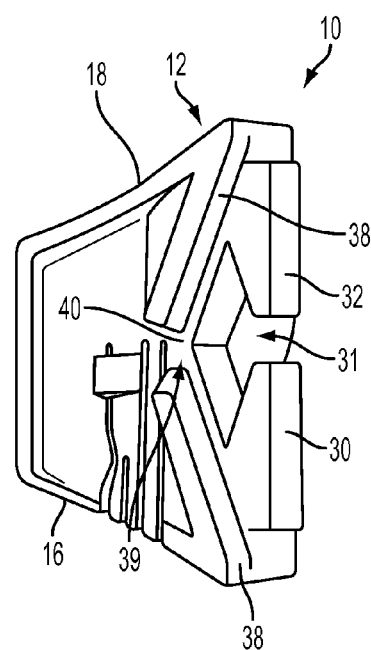
FIG. 3G is a top perspective view of the first end and the first surface of the suture management card of FIG. 3A.

As shown in FIGS. 3E-3G, a thickness t of the prongs 30, 32 can be less than the thickness T of the first end 12 from which they extend. As a result, shoulder 36 on which the suture filament can be seated when wrapped around the prongs 30, 32 is formed on the second surface 22 of the card 10, as shown in FIG. 3F. In the illustrated embodiment the shoulder 36 extends a small distance beyond the length L of the card 10. The reduced thickness t of the prongs 30, 32 also allows grooves or tracks 38 to be formed on the first surface 20 of the card 10, as shown in FIG. 3G, on which the filament forming the loop 52 can sit, as shown in FIG. 3B. The grooves or tracks 38 can extend diagonally from the first end 12, toward the second end 14, and meet at a vertex 39 substantially centered between the first and second sidewalls 16, 18. The grooves 38 can be in communication with a longitudinal seating groove 40 formed on the first surface 20 of the card 10, which itself can be configured to receive the knot 56 of the collapsible loop 52. The depths of the grooves 38 and the longitudinal seating groove 40 can be such that the any exposed portions of the suture 50 or knot 56 do not sit proud above the first surface 20, and thus are not easily chafed or frayed by contact with an outside object.

Below the longitudinal seating channel 40 are a plurality of slots 24 that work in harmony, along with the prongs 30, 32, to apply tension to the free limbs 54, 55 of suture filament extending from the knot 56 so that only a tension force that exceeds the ejection threshold tension can eject the loop 52 from the prongs 30, 32 of the suture management card 10. As shown, there is a first slot 24a, a second slot 24b, and a third slot 24c, each of which is formed in the first sidewall 16 and extends toward the second sidewall 18. The first and second slots 24a, 24b can be substantially parallel to each other and substantially perpendicular to a longitudinal axis M (FIG. 3A) extending the length of the card 10, with the second slot 24b being disposed closer to the second end 14 than is the first slot 24a. The third slot 24c can be disposed closer to the second end 14 than is the second slot 24b, and can include three separate portions that are in communication with each other. As shown, a first portion $24c_1$ of the third slot 24c can extend from the first sidewall 16 and toward the second sidewall 18, while being substantially parallel to the first and second slots 24a, 24b. A second portion $24c_2$ of the third slot 24c can be adjacent to and in communication with the first portion $24c_1$, and it can be substantially V-shaped with a vertex facing the first end 12. A third portion $24c_3$ of the slot 24c can be adjacent to and in communication with the second portion $24c_2$, and like the first portion $24c_1$ can be substantially parallel to the first and second slots 24a, 24b.

The first, second, and third slots 24a, 24b, and 24c can each terminate substantially in the center of the card 10 between the first and second sidewalls 16, 18. As shown, they define first and second deflectable tangs 28, 29, which can deflect above and below a plane extending through the card 10 that is substantially parallel to the first and second surfaces 20, 22. Because the slots 24a, 24b, 24c terminate substantially approximately at the center of the card between the first and second sidewalls 16, 18, the filament limbs 54, 55 extending from the knot 56 in the longitudinal seating groove 40 can be disposed in the slots 24a, 24b, 24c by extending in a substantially straight direction from the knot 56. The limbs 54, 55 can be selectively passed through the slots 24a, 24b, 24c to apply a frictional resistance to tension. For example, as shown in FIG. 3B, the filament limbs 54, 55 are passed from the longitudinal passageway 40, through the first slot 24a to the second surface 22 of the card 10, through the second slot 24b back to the first surface 20, and through the third slot 24c back to the second surface 22. In this configuration, the V-shaped second portion $24c_2$ of the third slot 24c can help keep the filament limbs 54, 55 from inadvertently being dislodged from the third slot 24c because a different angle of tension is needed to work the limbs 54, 55 through the third portion $24c_3$, over the vertex of the V-shaped second portion $24c_2$, and then out of the first portion $24c_1$ to disassociate those portions of the limbs 54, 55 with the suture management card 10.

The ejection threshold tension is the amount of force that must be exceeded to eject the loop 52 from the prongs 30, 32. A force in excess of the ejection threshold tension is generally applied to the loop 52 itself. The magnitude of the ejection threshold tension of the card 10 can principally be controlled by the configuration of the plurality of slots 24 and the suture 50 associated therewith. The configuration of the prongs 30, 32, such as the value of the angle α, can also affect the ejection threshold tension. The ejection threshold tension should be a value that will not generally be achieved by the application of an incidental force to the loop 52 during use. Preferably, only a purposeful application of force to the loop 52 should be sufficient to eject it from the prongs 30, 32. In some exemplary embodiments the ejection threshold tension can be in the range of about 3 Newtons to about 8 Newtons, and in one embodiment the threshold tension is about 5.5 Newtons. In other embodiments of a suture management card, a loop of suture can dislodge or eject from a card in a different manner than described above, for instance by including a sliding feature on the card that permits a user to eject the suture by sliding it off the card. A person skilled in the art will recognize that other techniques or features for disassociating the loop from the card can be adapted for use with the teachings provided herein, and that including such techniques or features on the card does not depart from the spirit of the present disclosure and the values described herein, e.g., the ejection threshold tension, can be adapted to apply to the appropriate features of the card. For example, a person skilled in the art will recognize the appropriate ejection threshold tension to use to remove a suture from a card in which the suture is designed to slide off the card after the ejection threshold tension is exceeded.

Figure 17A:
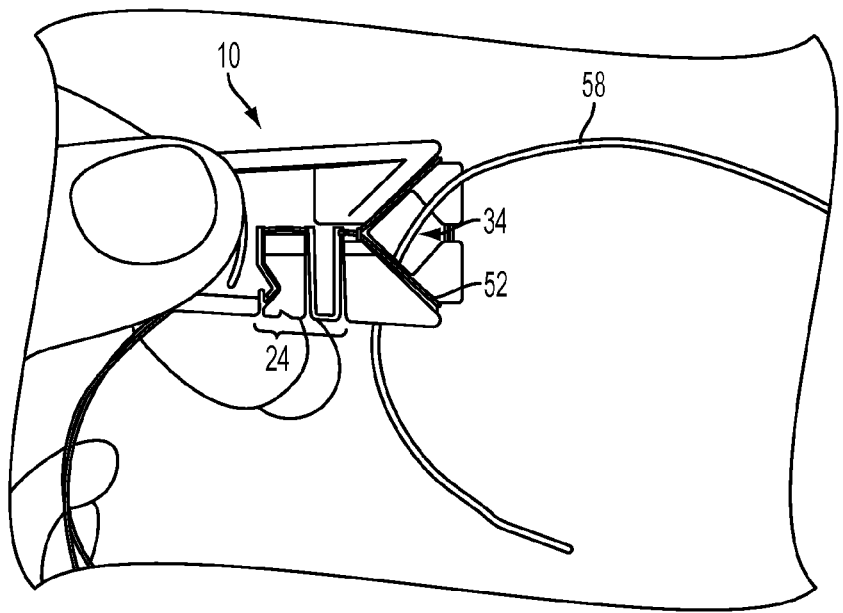
FIGS. 17A-17I are sequential views illustrating one exemplary embodiment for removing suture from the suture management card of FIG. 3A.
Figure 17B:
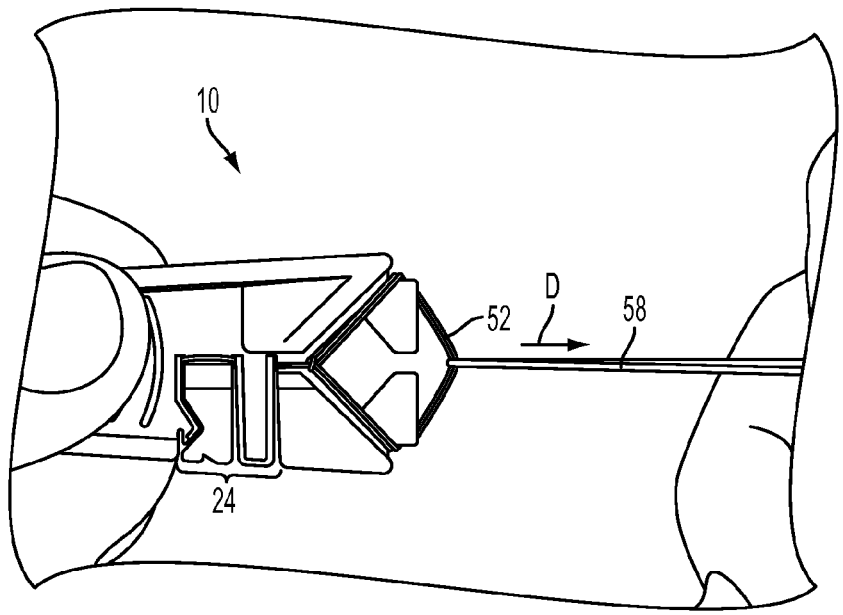
Figure 17C:
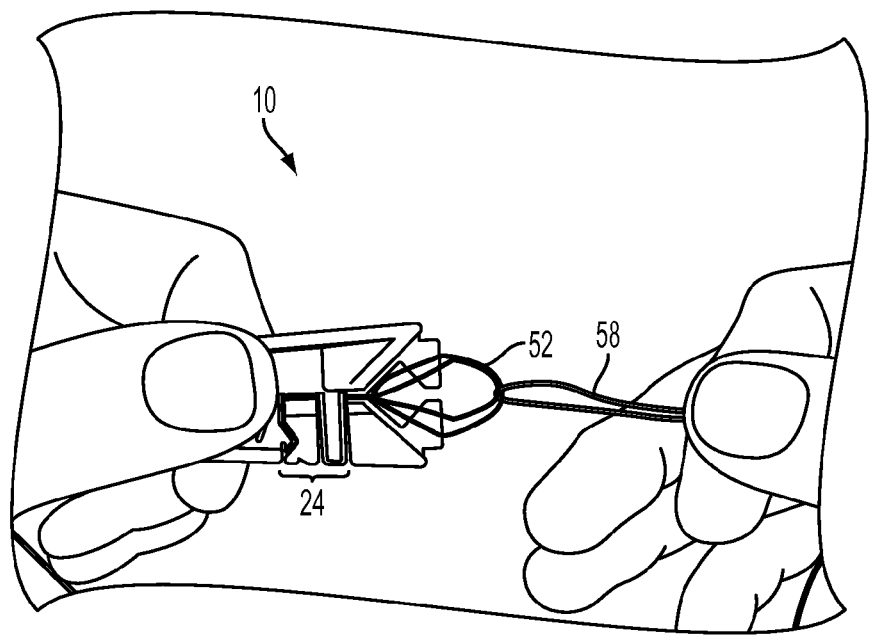
Figure 17D:
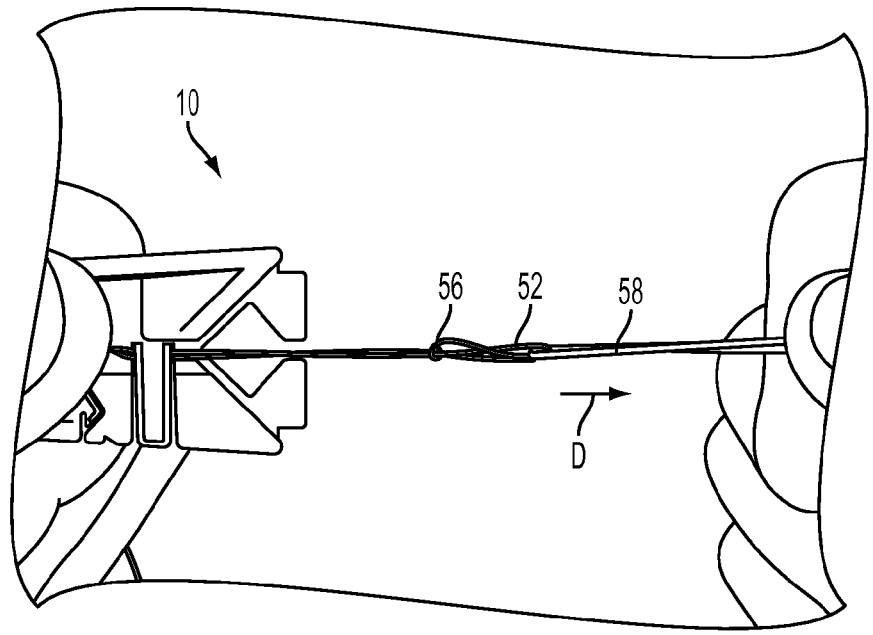
Figure 17E:
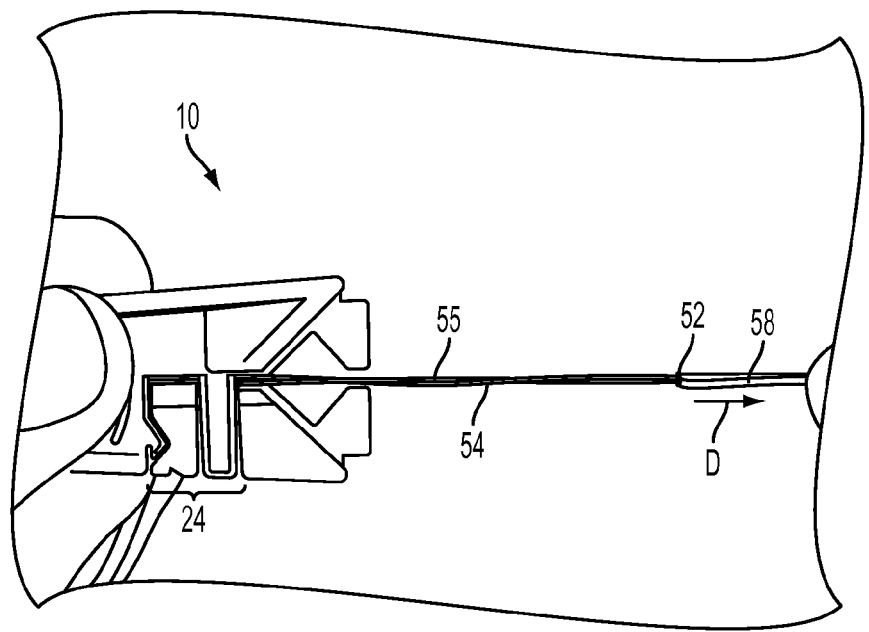

A collapsing threshold tension also exists, as discussed with more particularity with respect to FIGS. 17D and 17E. The collapsing threshold tension is the tension that, if exceeded, collapses the loop 52. A force in excess of the collapsing threshold tension is generally applied to the loop 52 to collapse it. The magnitude of the collapsing threshold tension of the card 10 can principally be controlled by the configuration of the plurality of slots 24, i.e., via friction through the slots 24, and the suture associated therewith. Its magnitude is generally greater than the ejection threshold tension and greater than a drag force of the knot 56 on the limbs 54, 55 running through it, thereby ensuring that the knot 56 collapses before the suture 50 slides through the slots 24. In some exemplary embodiments the collapsing threshold tension can be in the range of about 6 Newtons to about 15 Newtons, and in one embodiment the collapsing threshold tension is about 9 Newtons.

Figure 3H:
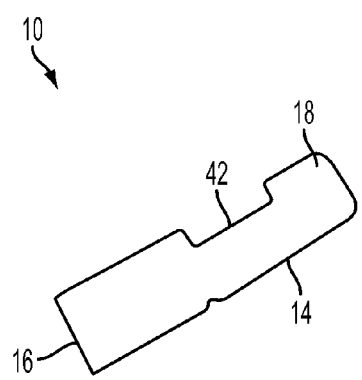
FIG. 3H is a bottom perspective view of a second end of the suture management card of FIG. 3A.
Figure 3I:
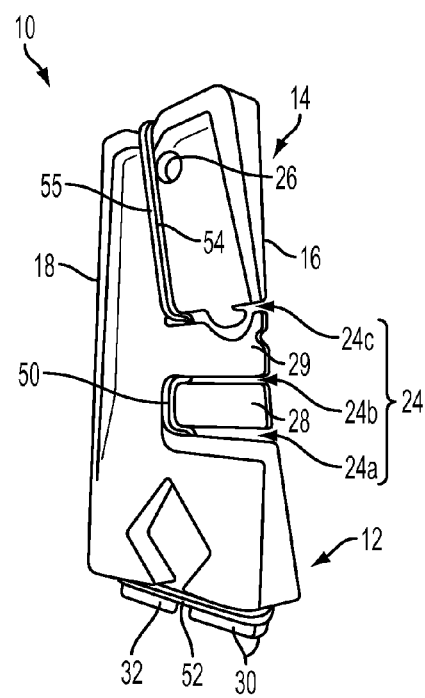
FIG. 3I is a top perspective view of the second surface of the suture management card of FIG. 3B.
Figure 3J:
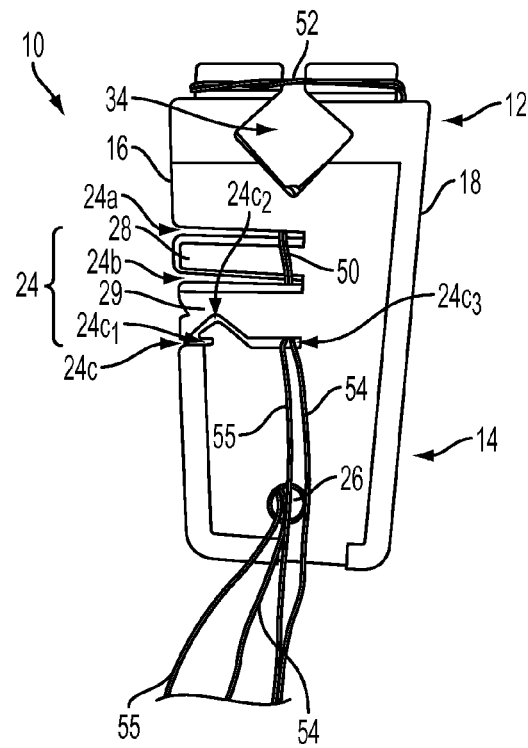
FIG. 3J is a bottom perspective view of the second surface of the suture management card of FIG. 3B, with the suture passing through a thru-hole of the second end.
Figure 3K:
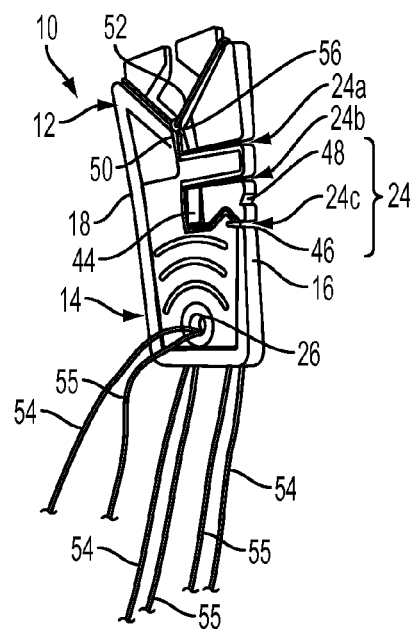
FIG. 3K is a top perspective view of the first surface of the suture management card of FIG. 3J.

As shown in FIG. 3H, a slot 42 can be formed in the second surface 22 of the terminal end of the second end 14 to receive the limbs 54, 55 extending from the last slot 24c. The slot 42 can also receive portions of the limbs 54, 55 disposed in a sleeve 58 when a sleeve 58 returns back toward the card 10 after being coupled to an anchor, as described below. The slot 42 protects the limbs 54, 55 and sleeve 58 from extending substantially above the second surface 22 as the thickness T of the first sidewall 16 increases while approaching the second end 14. Thus, as shown in FIG. 3I, the limbs 54, 55 can sit against the second surface 22, within the slot 42, and be protected against unintended fraying or chafing. In the illustrated embodiment, the slot 42 extends between a substantial center portion of the card 10, toward the second sidewall 18, terminating prior to the second sidewall 18, although other configurations and locations are possible without departing from the spirit of the disclosure.

In some embodiments, the slot 42 can receive an initial portion of the limbs 54, 55 that extend from the third slot 24c, as illustrated in FIG. 3I, and it can also receive a distal portion of the limbs 54, 55 that return from an anchor, as illustrated in FIG. 3J. In some embodiments, the limbs 54, 55 can be disposed in a sleeve 58 when they pass through the slot 42, as described below.

An opening 26 proximal of the slot 42 can be formed adjacent the second end 14. The opening 26 can be configured to receive the distal portion of the filament limbs 54, 55 that return to the card 10 after first being coupled to an anchor. In the illustrated embodiment, the opening 26 is a thru-hole that extends between the first and second surfaces 20, 22, substantially centered between the first and second sidewalls 16, 18. As shown in FIGS. 3J and 3K, the distal portion of the filament limbs 54, 55 can pass through the opening 26. These limbs 54, 55 can be retained in a handle of an inserter tool when the card 10 is disposed in an inserter tool, and can be accessible by the surgeon when the card 10 is removed from the inserter tool, as described in further detail below.

The first and second surfaces 20, 22 of the card 10 can include a number of different features to assist a surgeon in using the card 10, for instance by helping to prevent the misuse of the card by disassociating portions of suture filament from the card earlier than desired. As shown in FIGS. 3A and 3B, some of these features include a raised surface 44, a catch slot 46, and a boot notch 48, the purposes of which are described below in greater detail with respect to the second suture management card 10' and shown in FIGS. 8-11. Optionally, one or more raised ridges 49 can be formed on one of the first or second surfaces 20, 22 of the card 10. In the illustrated embodiment, four raised ridges 49 are formed on the first surface 20 between the third slot 24c and the thru-hole 26, with the ridges 49 having a decreasing arc length and an increasing radius of curvature as they approach the distal end 14 of the card 10. As shown, the distal-most raised ridge 49 can have a radius of curvature that substantially tracks the arc of the opening 26. The raised ridges 49 can improve a surgeon's grip on the card 10 when the card 10 is being held by the surgeon during ejection of the loop 52 and the subsequent disassociation of the suture filament 50 from the card 10. Additionally, in instances in which the ridges 49 are formed only on one of the two surfaces 20, 22, the ridges 49 can help a surgeon distinguish between the first and second sides of the card 10 by tactile feedback.

Figure 3L:
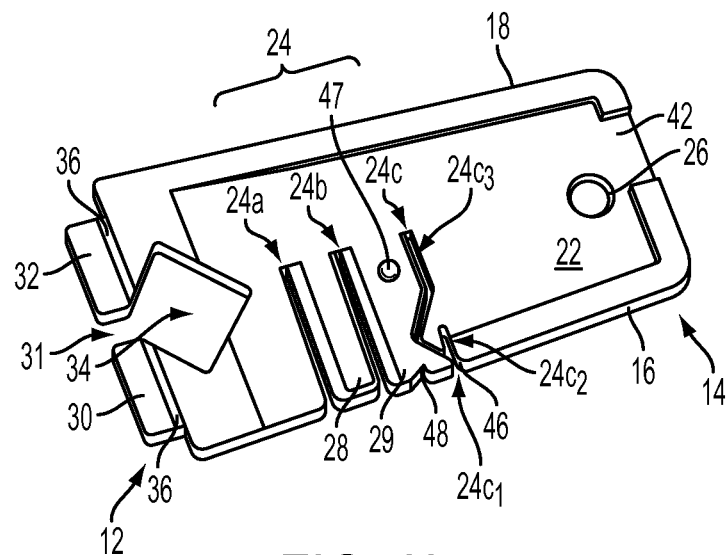
FIG. 3L is a bottom perspective view of the second surface of the suture management card of FIG. 3A.
Figure 4:
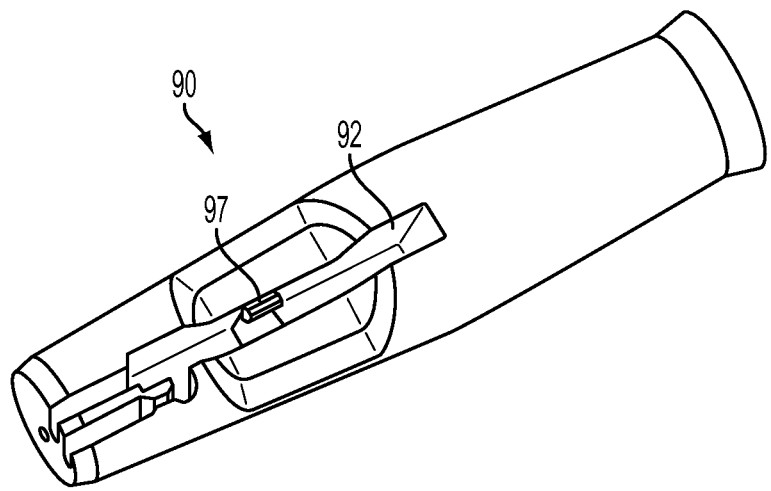
FIG. 4 is a top perspective view of the handle of FIG. 2.

Features to assist with insertion of the card into an inserter tool can also be included on the first and second surfaces 20, 22. As shown in FIG. 3L, the second surface 22 can include a protrusion 47 formed thereon. The protrusion 47 can be any shape or size, but in the illustrated embodiment it is a raised hemispherical portion formed on the second surface 22. The protrusion 47 can be configured to be complementary to a retention feature located within the slot 92 of the handle 90 of the inserter tool 80 to form a snap fit. FIG. 4 illustrates one such complementary retention feature 97. The retention feature 97 is a rectangular boss having two chamfered edge surfaces 97a, 97b. The boss 97 can be disposed in the slot 92 at a location such that when the protrusion 47 passes the second chamfer 97b, the second sidewall 18 is substantially flush with the handle 90.

Figure 5:
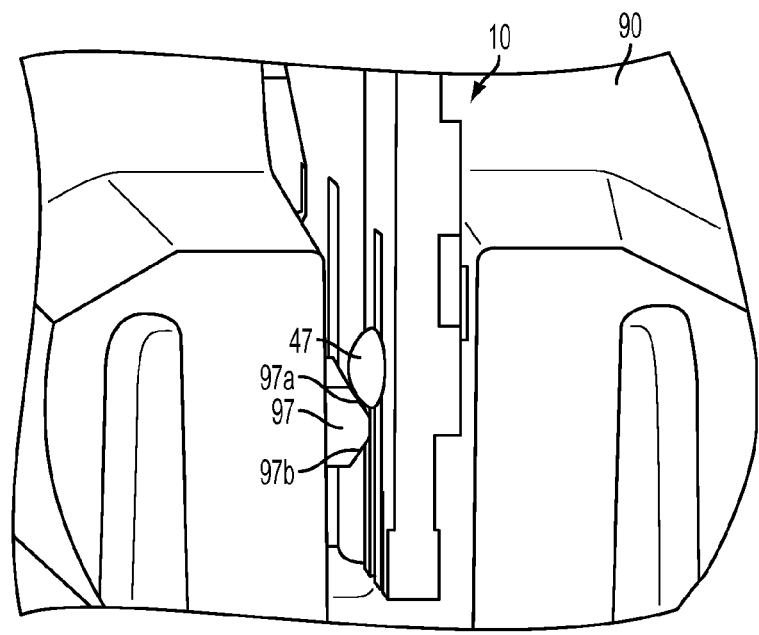
FIGS. 5-6 are sequential views illustrating one exemplary embodiment for installing the suture management card of FIG. 3L into the handle of FIG. 4.
Figure 6:
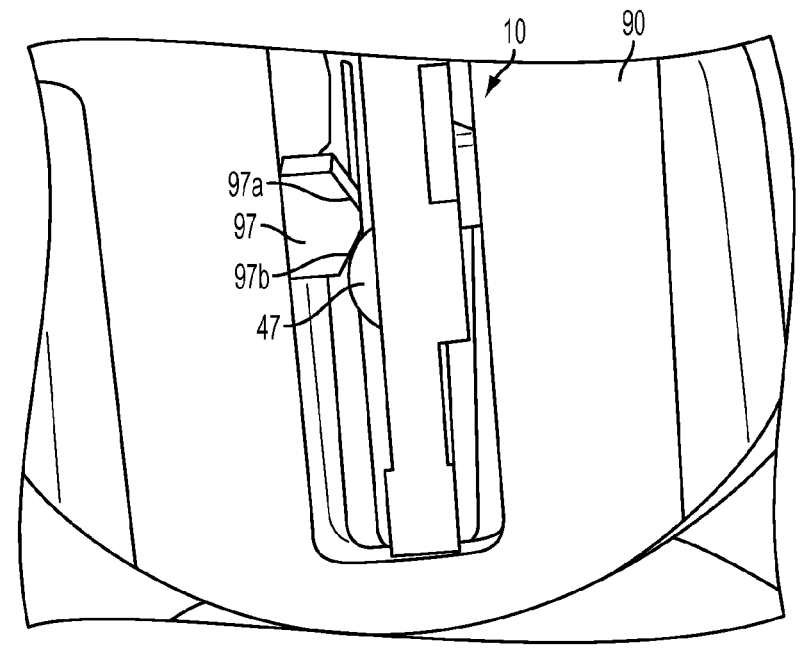

As shown in FIGS. 5 and 6, as the card 10 is inserted into the handle 90, the protrusion 47 slides over the first chamfer 97a and to the second chamfer 97b to secure the card 10 in the slot 92. When the protrusion 47 passes the second chamfer 97b, an audible sound can optionally provide feedback to the surgeon to confirm that the card 10 is secured in the handle 90. As the card 10 is pulled out of the handle 90, the protrusion 47 slides back over the second chamfer 97b, past the first chamfer 97a, and out of the handle 90.

A variety of different suture filaments having different features and functions can be used in association with suture management card disclosed herein. One skilled in the art will appreciate that such sutures can be made of a variety of suitable materials. Moreover, the suture filaments can be of different types, including but not limited to a cannulated filament, a braided filament, and a mono filament. The type, size, and strength of the filament can depend, at least in part, on the other materials of the system, including the material (s) of the suture management card, the tissue and other components through which it will be passed or coupled to, and the type of procedure in which it is used. As shown in FIG. 3B, in one exemplary embodiment, the suture filament 50 has a sliding knot 56 formed therein that defines a collapsible loop 52. The loop is formed from first and second limbs 54, 55 of the filament 50. Extending from the side of the knot 56 opposite the loop 52 can be first and second suture free filaments limbs 54, 55. These are "free" limbs because they are not the portion of the limbs 54, 55 that forms the loop 52. A person skilled in the art will recognize a number of different by which the sliding knot 56, and resulting loop 52 and free limbs 54, 55, can be formed. By way of non-limiting example, the knot 56 can be a Buntline Hitch, a Tennessee slider, a Duncan Loop, or a Hangman's Noose.

In one exemplary embodiment the filament is a #0 filament (about 26 gauge to about 27 gauge), such as an Orthocord™ filament that is commercially available from DePuy Mitek, LLC, 325 Paramount Drive, Raynham, Mass. 02767, or an Ethibond™ filament that is commercially available from Ethicon, Inc., Route 22 West, Somerville, N.J. 08876. The thickness of the filament should provide strength in the connection but at the same time minimize the trauma caused to tissue through which it passes. In some embodiments the filament can have a size in the range of about a #5 filament (about 20 gauge to about 21 gauge) and about a #5-0 filament (about 35 gauge to about 38 gauge). Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed.

Optionally, a flexible sleeve can be provided for encapsulating at least a portion of the first and second suture filament limbs 54, 55. Although not illustrated in FIGS. 3A-3J, FIG. 13 illustrates a sleeve 58 disposed around a portion of the filament limbs 54, 55 that extends distally from the knot 56. In one exemplary embodiment, the sleeve begins at a location of the filament limbs 54, 55 that extends distally along the inserter tool shaft 82 prior to the limbs 54, 55 reaching the anchor 100, and then covers the remaining portions of the limbs 54, 55 such that terminal ends of the limbs 54, 55 terminate before the terminal end of the sleeve 58. The sleeve can assist in managing the filament limbs 54, 55 as they pass through and around the anchor 100, proximally up the shaft 82 of the inserter tool 80, back into the suture management card 10, and into the handle 90 of the inserter tool 80. Additionally, the sleeve 58 can be configured to have a smooth surface so that it can easily pass through tissue, thus easing trauma caused by passing the construct through tissue. The sleeve can be removable, and can be removed at any desired during time during a repair procedure.

The sleeve can be made from a wide variety of biocompatible flexible materials, including a flexible polymer or it can be another filament. In one embodiment, the sleeve is made of a polymeric material. In another embodiment, the sleeve is a flexible filament, such as a braided suture, for example Ethibond™ #0 filament or Orthocord™ #2 filament, which is typically braided at sixty picks per 2.54 centimeters. For use as a sleeve, a more relaxed braid of approximately thirty to forty picks per 2.54 centimeters is preferred, more preferably about 36 picks per 2.54 centimeters. If the sleeve material is formed about a core, preferably that core is removed to facilitate insertion of the filament limbs, which may themselves be formed of typical suture such as Orthocord™ #0 suture or #2 suture braided at sixty picks per 2.54 centimeters. Additional convenience can be provided by perceptible indicators on the sleeve such as different markings, colors, diameters, braid or design patterns, or other tactile or visual indicia, especially if multiple tissue attachments or anchors are utilized.

A sliding knot can be formed in a filament to define a loop using a variety of techniques known to those skilled in the art, including but not limited to forming a Buntline Hitch, a Tennessee slider, a Duncan Loop, or a Hangman's Noose. As shown in FIGS. 7A and 7B, a filament 50' can be folded approximately in half and can have a double over-hand knot 52' formed therein. Tails 54', 55' of the filament 50' can be passed through the knot 52' to form a loop 56'. The knot 52' can then be tightened around the tails 54', 55' to form the collapsed sliding knot 52' using a variety of techniques known to those skilled in the art. In one exemplary embodiment, illustrated in FIG. 7C, a dowel 51' or other object can be disposed in the loop 56' to prevent the loop 56' from fully collapsing when a force in a direction J is applied to the tails 54', 55'. As a result, when the force in the direction J is applied to the tails 54', 55', the knot 52' collapses, resulting in the loop 56' extending from one side of the knot 52' and the tails 54', 55' extending from the other side of the knot 52'.

Figure 7D:
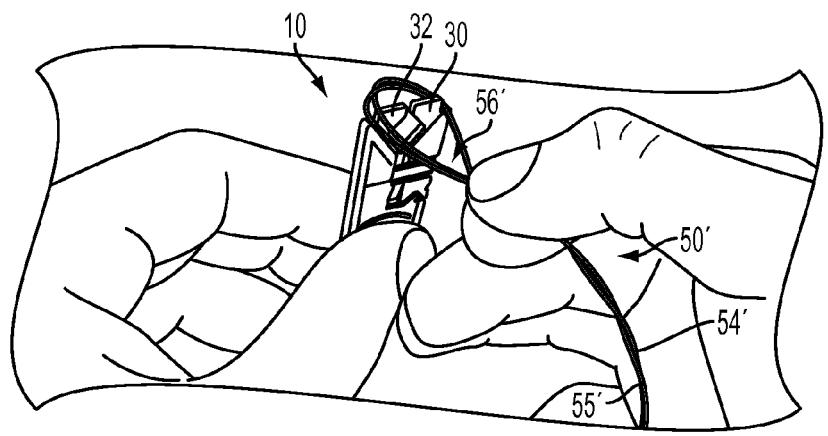
FIGS. 7D-7I are sequential views illustrating one exemplary embodiment for installing the suture of FIG. 7C onto the first suture management card of FIG. 1.
Figure 7E:
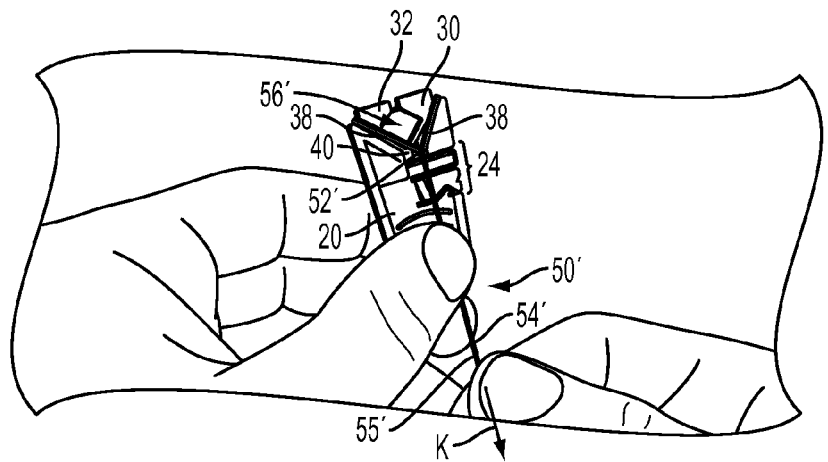

The filament 50' having the loop 56' and tails 54', 55' can be attached to a suture management card. FIGS. 7D-7I illustrate one exemplary embodiment of coupling the filament 50' to the first suture management card 10. As shown in FIG. 7D, the loop 56' can be placed around the prongs 30, 32 to create an initial attachment point between the filament 50' and the card 10. A force in a direction K can be applied to the tails 54', 55' to tighten the loop 56' around the prongs 30, 32, as shown in FIG. 7E. As the loop 56' tightens, the filament 50' can be manipulated so that the loop 56' sits in the grooves 38 and the knot 52' sits in the longitudinal seating groove 40, thereby reducing the risk of the filament 50' chafing or fraying.

Figure 7F:
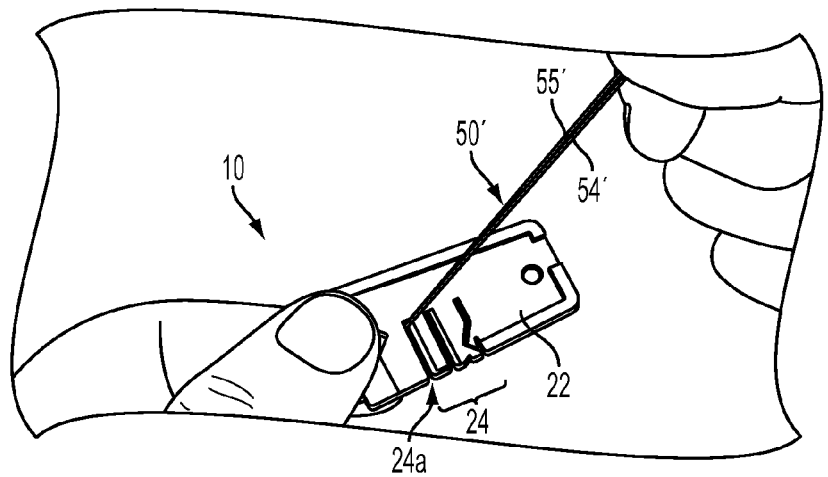
Figure 7G:
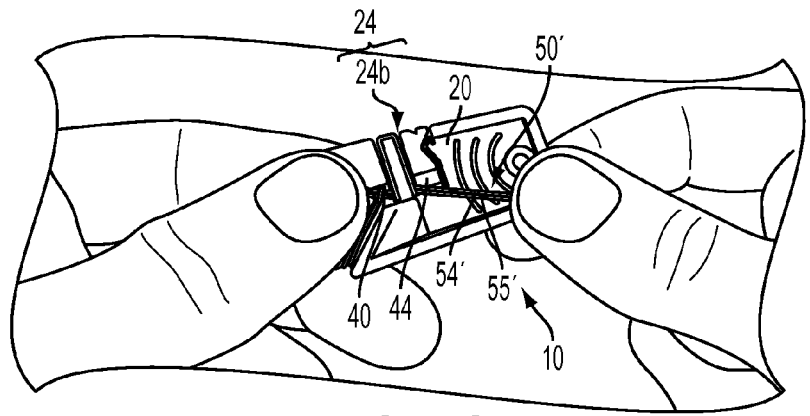

As shown in FIG. 7F, the tails 54', 55' can then be disposed in the slots 24. The tails 54', 55' can first be disposed in the first slot 24a, passing from the first surface 20 toward the second surface 22. In one embodiment the tails 54', 55' are slid to a terminal end of the slot 24a so that the filament 50' extends approximately in-line with the longitudinal channel 40 of the card 10. As shown in FIG. 7G, the tails 54', 55' can then be disposed in the second slot 24b, passing from the second surface 22 toward the first surface 20. The tails 54', 55' can be slid to a terminal end of the slot 24b so that the filament 50' continues to extend in an approximately straight configuration from the longitudinal channel 40.

Figure 7H:
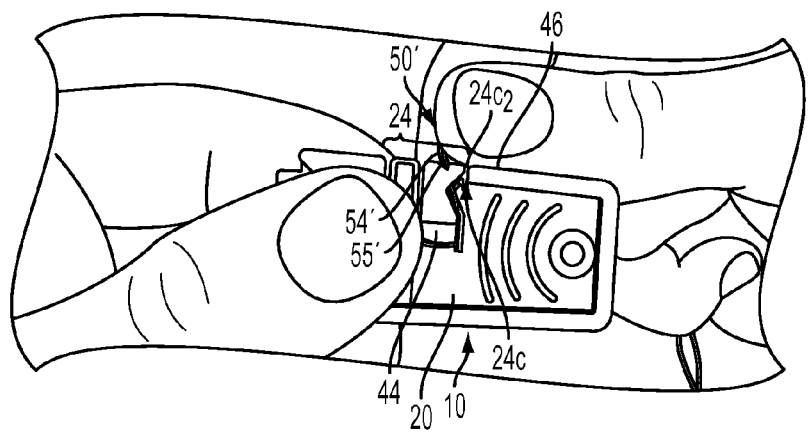
Figure 7I:
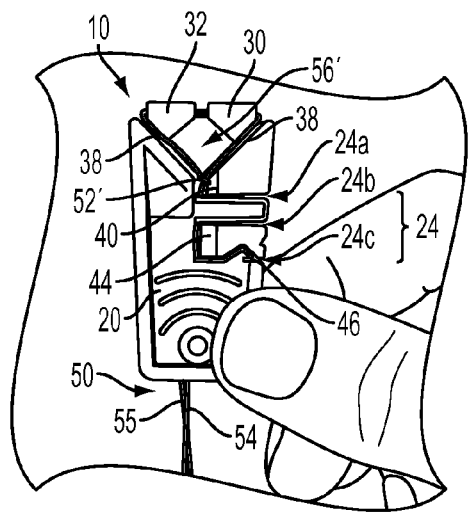
Figure 8:
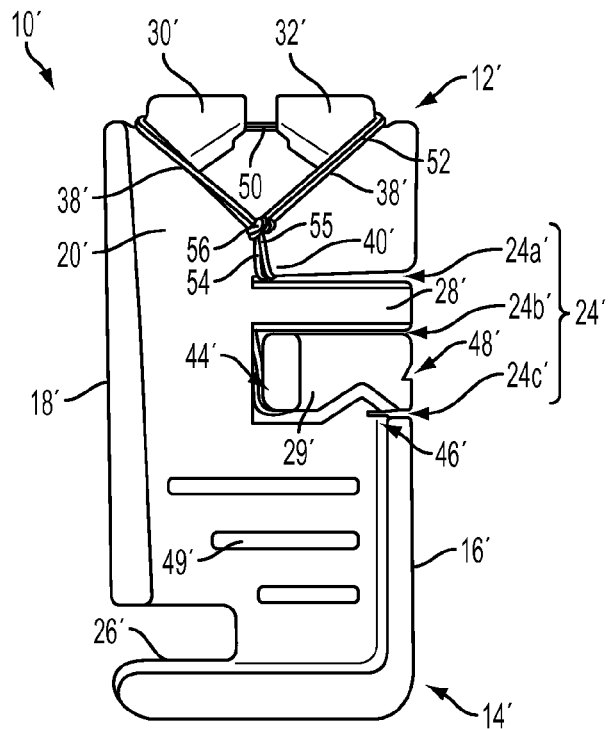
FIG. 8 is a top perspective view of the second suture management card of FIG. 1.

As shown in FIG. 7H, the tails 54', 55' can extend adjacent to and behind the raised surface 44 and can be passed into the third slot 24c. The tails 54', 55' once again extend from the first surface 20 and toward the second surface 22, and they can be manipulated through the third slot 24c so as not to get caught in the catch slot 46 and so they pass up and over the second, V-shaped portion 24c₂ of the third slot 24c. As shown in FIG. 7I, the tails 54', 55' can be slid to a terminal end of the slot 24c, again allowing the filament 50' to continue to extend in an approximately straight configuration from the longitudinal channel 40. Further, because the filament 50' is disposed adjacent to and behind the raised surface 44, the raised surface 44 can be effective to prevent unintentional off-loading of the filament 50' from the card 10, as described below with respect to FIG. 9. With the filament 50' coupled to the card 10, the filament 50' and card 10 can be used in manners consistent with the descriptions contained herein. A person skilled in the art will understand how these same steps for associating a filament with a suture management card can be adapted for use with the suture management card 10'.

FIGS. 8-11 illustrate the second exemplary embodiment of a suture management card 10'. This second suture management card 10' has many similar features to that of the first suture management card 10. It can have a substantially polygonal shape, as shown a trapezoidal shape, with a proximal or first end 12' and a distal or second end 14', a first sidewall 16' and a second sidewall 18' extending between the first and second ends 12', 14', and a first surface 20' and a second surface 22' (not shown). The size and shape of the card 10', as well as the materials used to make the card 10', can be substantially similar to that of the first card 10. For example, a width and thickness of the second card 10' can vary over portions of a body of the card 10' in a manner similar to as described with respect to the card 10.

The suture management card 10' can also include many of the same features as the suture management card 10, including first and second prongs 30', 32' for holding open a loop 52 of suture filament 50, grooves 38' and a shoulder 36' (not shown) along which a length of the filament loop 52 can be disposed, a longitudinal seating channel 40' in which a knot 56 formed in the suture filament 50 can be disposed, a plurality of slots 24' (24a', 24b', 24c') disposed distal of the longitudinal seating channel 40' for applying tension to free limbs 54, 55 of suture filament 50 extending from the knot 56, and first and second deflectable tangs 28', 29' formed by the slots 24'. Additional features of the card 10' that are similar to features in the card 10 include a slot 42' (not shown) formed in the terminal end of the second end 14' to receive filament limbs 54, 55 extending from the last slot 24c', an opening 26' proximal of the slot 42' for receiving a distal portion of the filament limbs 54, 55 that return to the card 10' after first being coupled to an anchor, and features to assist a surgeon in using the card, including a raised surface 44', a catch slot 46', a boot notch 48', ridges 49' formed on a first surface 20' of the card 10', and a protrusion 47' (not shown) formed on the second surface 22' to assist with insertion of the card 10' into an inserter tool. While many of these features have similar configurations as their equivalent features of the suture management card 10, some differences are described below. A person having skill in the art will recognize that these differences can be interchangeably incorporated into the two suture management cards 10, 10', or other similar devices, without departing from the spirit of the present disclosure.

The grooves or tracks 38' formed in the first end 12' of the card 10' and extending diagonally from the first end 12' and toward the second end 14' are different than the grooves 38 of card 10 in that these grooves 38' extend deeper into the first surface 20'. Ridges and bosses are included along the path where the suture filament 50 runs, which makes it more difficult to pull the filament 50 out of the grooves 38' and mistakenly pull the loop 52 off the prongs 30', 32'. This configuration generally prevents a surgeon from using his or her finger to access the filament 50 disposed in the grooves 38' and thus the filament 50 typically exits the grooves 38' only after a force greater than the ejection threshold tension is applied to eject the loop 52 from the prongs 30', 32'. Similar to the grooves 38 of the card 10, the grooves 38' are in communication with the longitudinal seating groove 40', which can receive the sliding knot 56 formed in the suture filament 50.

While the second suture card 10' includes an opening 26' formed in the second end 14', the opening 26' is different than the opening 26 in that it is an open-ended slot rather than a closed thru-hole. As shown, the opening 26' is a slot formed in the second sidewall 18, extending towards the first sidewall 16, and terminating just short of a center portion between the first and second sidewalls 16, 18. As described in greater detail with respect to FIGS. 16A-16D, this design allows the distal portion of the filament limbs 54, 55 to be readily accessed by the surgeon without having to take a separate action to pull the distal portion of the filament limbs 54, 55 out of the opening.

The raised ridges 49' formed on the first surface 20' serve a similar purpose as the raised ridges 49 of the card 10. They can improve a surgeons grip on the card 10', and they can also help a surgeon easily know the difference between the two sides 20', 22' of the card 10' based on tactile feedback. The ridges 49' in the illustrated embodiment include three substantially straight grooves that decrease in length as they approach the distal end 14'.

Figure 9:
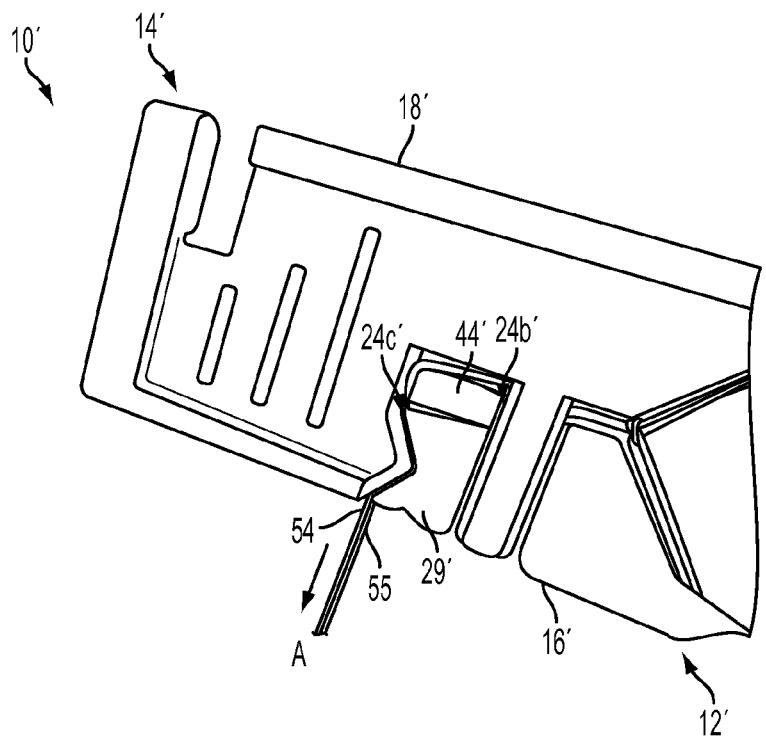
FIG. 9 is a top perspective view of the suture management card of FIG. 8, illustrating a raised portion formed thereon.
Figure 10:
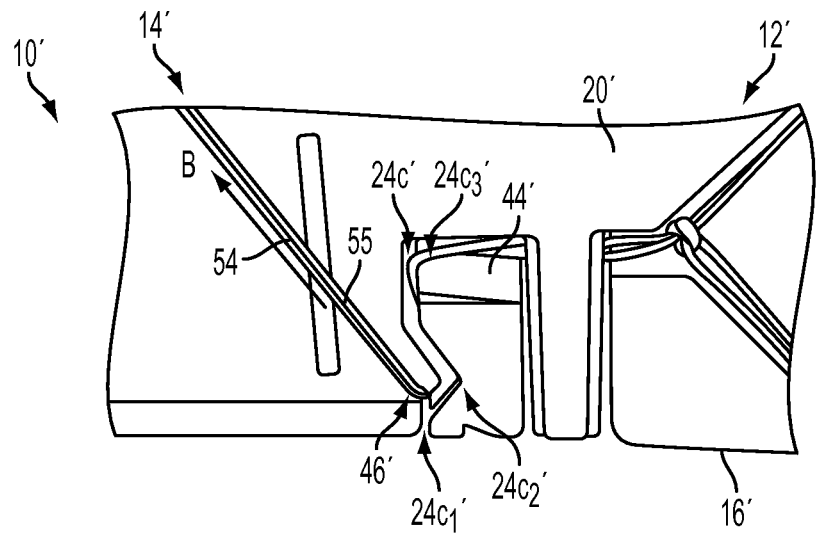
FIG. 10 is a side perspective view of the suture management card of FIG. 8, illustrating a catch slot formed therein.
Figure 11:
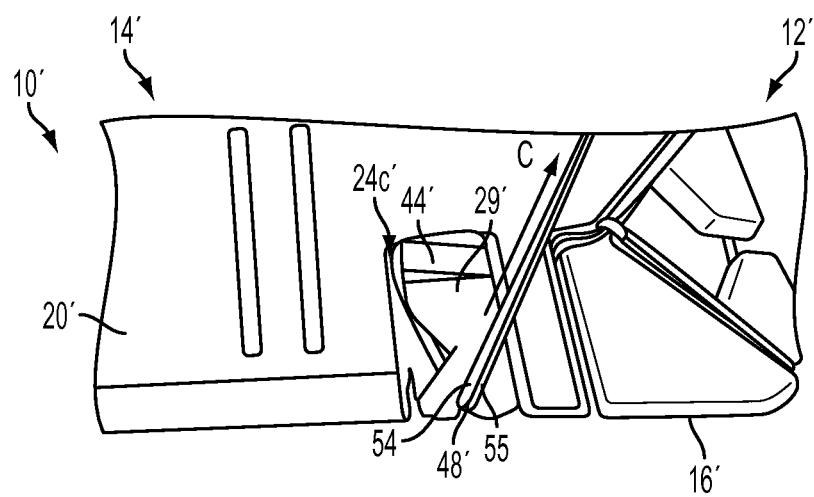
FIG. 11 is a side perspective view of the suture management card of FIG. 8, illustrating a boot notch formed therein.

Features designed to assist a surgeon in using the card 10', and in particular helping to prevent the misuse of the card 10' by disassociating portions of the suture filament 50 from the card 10' earlier than desired, are illustrated with particularity in FIGS. 9-11. FIG. 9 helps illustrate a benefit of the raised portion 44' disposed on the second deflectable tang 29'. The raised portion 44' can have a variety of shapes, but in the illustrated embodiment it is a pyramid-shaped ramp that increases in height from the second slot 24b' to the third slot 24c'. The raised portion 49' can be raised with respect to the first surface 20' between about 0.5 to about 2 millimeters, and in the illustrated embodiment a peak height of the raised portion 44' is about 1 millimeter. As shown, when tension is applied in an approximate direction A, the filament limbs 54, 55 are prevented from off-loading via the third slot 24c' because the raised portion 44' resists the tension. Instead the filament limbs 54, 55 are held against the root of the third slot 24c'.

FIG. 10 illustrates another feature of the suture management card 10' that helps prevent inadvertent off-loading of the suture. This feature is a catch slot 46' formed in the body of the card 10', extending off an entry way of the third slot 24c'. As shown, the catch slot 46' extends from a first portion $24c_1$' of the third slot 24c', toward the second sidewall 18' (not shown), and inward of a base of a V-shaped second portion $24c2$ of the third slot 24c'. When a surgeon brings the filament limbs 54, 55 around from the second surface 22' (not shown) of the body, over to the first surface 20', and applies tension to the filament limbs 54, 55 in an approximate direction B as shown, the catch slot 46' is designed to catch the filament limbs 54, 55 and absorb the applied tension. If the catch slot 46' was not present, the force could allow the filament limbs 54, 55 to slide over the V-shaped second portion $24c_2$, to a third portion $24c_3$' of the third slot 24c', in which the filament limbs 54, 55 are disposed, and then the filament limbs 54, 55 could be removed from the third slot 24c'. While a length of the catch slot 46' can be depend, at least in part, on the dimensions of the other features of the card, the size of the filament, and the type of procedure in which the card and suture are being used, in one exemplary embodiment a length of the catch slot 46' is in the range of about 0.5 millimeters to about 3 millimeters, and in one embodiment it is about 1 millimeter.

FIG. 11 illustrates a third feature of the suture management card 10' designed to help prevent inadvertent off-loading of a suture. This feature is a boot notch 48' formed in the first sidewall 16' of the second deflectable tang 29'. The notch 48' can have a variety of shapes, but as shown it is substantially triangular in shape. The boot notch 48' is designed to prevent inadvertent offloading when filament limbs 54, 55 are brought from the second surface 22' (not shown) and around to the first surface 20'. More particularly, if no boot notch 48' is present, as the filament limbs 54, 55 are brought around in this manner, they can supply a force in an approximate direction C sufficient to deflect the second deflectable tang 29' a distance that allows the filament limbs 54, 55 to escape the third slot 24c'. However, when the filament limbs 54, 55 are caught by the boot notch 48', the tang 29' is not generally able to deflect enough to cause inadvertent off-loading because the notch 48' can catch the filament limbs 54, 55 before they are allowed to completely bridge the gap and escape when the tang 29' deflects.

Figure 12:
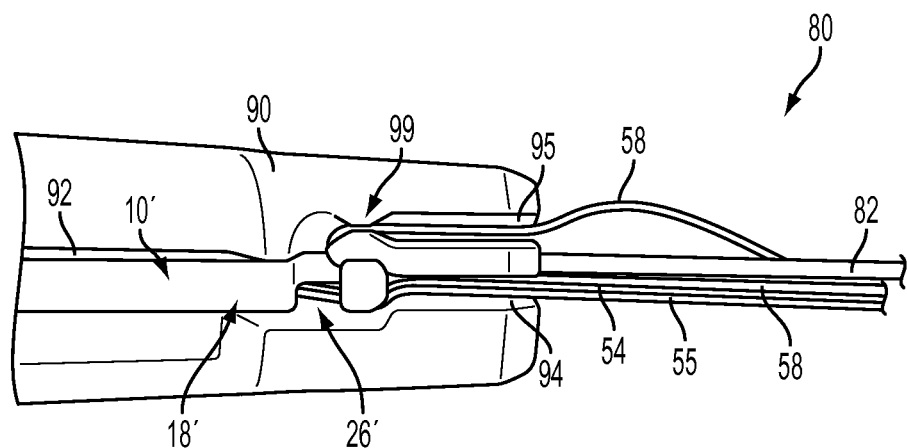
FIG. 12 is a top perspective view of the inserter tool of FIG. 1 and the suture management card of FIG. 8.
Figure 13:
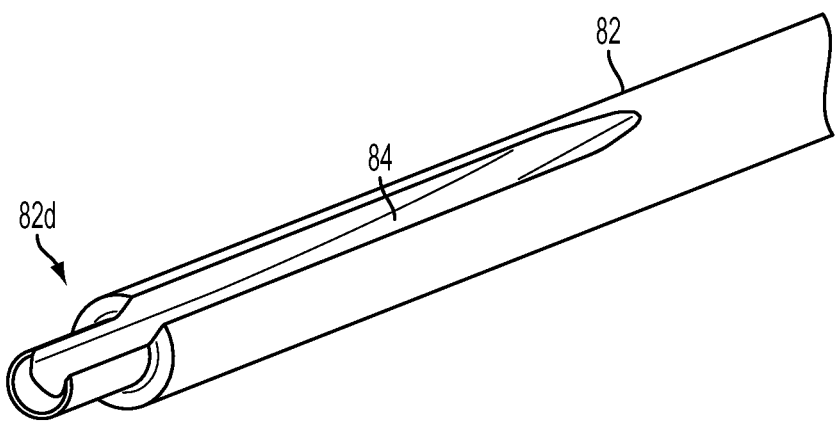
FIG. 13 is a perspective view of a distal end of a shaft of the inserter tool of FIG. 1.

FIG. 12 illustrates the second suture management card 10' disposed in the handle 90 of the inserter tool 80. The card 10' can be inserted into the handle 90 in a manner similar to the card 10, including, by way of non-limiting example, with an auditory feedback during a snap fit to provide assurance that the card 10' is properly situated in the handle 90. As shown, the open-ended slot 26' of the card 10' can face out of the handle 90 such that when the card 10' is removed from the handle 90, the filament limbs 54, 55 disposed therein are pushed out by the slot 26' and become readily available for use by the surgeon.

As shown, the handle 90 includes first and second suture-receiving slots 94, 95. While the slots 94, 95 can have many different shapes and configurations, in the illustrated embodiment the first slot 94 has a relatively fixed width and depth, and is generally configured to receive the filaments limbs 54, 55 as they initially pass off the card 10', through the slot 42' (not shown) formed in the second end 14', and toward the anchor. Additionally, the slot 94 can also receive the filament limbs 54, 55 after they extend proximally toward the handle 90, from the anchor with which the limbs 54, 55 are coupled. In the illustrated embodiment, the limbs 54, 55 extending toward the anchor are not initially encapsulated by a sleeve, but the limbs 54, 55 extending back toward the handle 90 are encapsulated by a sleeve 58. The relatively fixed width of the slot 94 can generally be wide enough so that the filament limbs 54, 55 disposed therein loosely extend therethrough but are not held in place by the slot 94. In one exemplary embodiment, a width of the slot 94 is in the range of about 2 millimeters to about 5 millimeters, and in one embodiment the width is about 3 millimeters, while a depth is in the range of about 4 millimeters to about 10 millimeters, and in one embodiment the depth is about 6 millimeters. The length is generally the length from the handle slot 92 to the end of the handle 90, which in one exemplary embodiment is in the range of about 0.5 centimeters to about 3 centimeters, and in one embodiment is about 1.2 centimeters.

The second suture-receiving slot 95 is different than the first slot 94 in that it includes a pinch point 99 that is configured to engage and hold the sleeve 58 in place when the card 10' is disposed in the handle 90 during anchor implantation, and help strip the sleeve out of the slot 95 when the card 10' is removed from the handle 90. The pinch point 99 is defined by a portion of the slot 95 having a reduced depth and width. Thus, while a distal end 95d of the second slot 95 can have a depth and width similar to that of the first slot 94, in one embodiment a depth can become shallower on each side of the pinch point 99. The depth can decrease progressively so as not to have a sharp edge against which the suture filament disposed therein frays or chafes. Likewise, a width of the slot 95, particularly at the pinch point 99, can become smaller so the sleeve 58 can actually be grasped by the pinch point 99. As shown, the width associated with the pinch point 99 can become progressively smaller, although the decrease in depth of the second slot 95 does not necessarily coincide with the decrease in a width of the slot 95. The width of the pinch point 99 can be such that it holds the sleeve 58 in place during anchor insertion, but allows the limbs sleeve 58 to be pulled out of the handle 90 at the same time the card 10' is pulled out. In one exemplary embodiment, a smallest width of the pinch point 99 is in the range of about 0.25 millimeters to about 0.5 millimeters, and in one embodiment is about 0.3 millimeters, while a smallest depth of the pinch point 99 is in the range of about 2 millimeters to about 5 millimeters, and in one embodiment is about 3 millimeters. In the illustrated embodiment, a length of the second slot 95 preceding the pinch point 99 is about the same as the length of the entire first slot, while the pinch point 99 adds a length to the slot in the range of about 0.5 centimeters to about 2 centimeters, and in one exemplary embodiment it adds a length to slot that is about 0.8 centimeters.

The handle 90 can have any size and shape that is generally useful for a surgeon during a surgical procedure. In one exemplary embodiment, the handle 90 is substantially cylindrical, having a diameter in the range of about 1.5 centimeters to about 4 centimeters, for instance about 2.5 centimeters, and a length in the range of about 8 centimeters to about 16 centimeters, for instance about 12 centimeters. The handle 80 can be made out of materials typically used for medical device insertion tools, such as polymers or metals. In one exemplary embodiment, the handle 80 is made of a thermoplastic such as acrylonitrile butadiene styrene (ABS).

The shaft 82 of the inserter tool 80 can extend distally from the handle 90 and can be generally elongate. A distal end 82d of the shaft 82 can be configured to mate to an anchor 100 with which the suture filament 50 will be coupled. In the illustrated embodiment of FIG. 13, a terminal portion of the shaft's distal end 82d includes a reduced circumference for receiving the suture anchor 100. Optionally, a groove 84 can be formed in the distal end 82d to help guide the filament 50 into a bore 102 of the anchor 100 and also to protect the filament 50 from unintended fraying or chafing. As shown, the groove 84 increases in depth as it extends distally, extending into the reduced circumference portion of the shaft 82 that couples with the anchor 100. The depth of the groove 84 can depend on the size of the filament 50 that will be disposed therein, and a person skilled in the art is able to determine a desirable depth based on the other components of the system and the type of surgical procedure being performed. The length of the shaft 82 can likewise depend on the other components of the system and the type of surgical procedure being performed, but in one embodiment a length of the shaft 82 is in the range of about 18 centimeters to about 30 centimeters, and in one embodiment is about 24 centimeters. Any number of materials can be used to form the shaft 82, including biocompatible materials and metals. In some exemplary embodiments, the shaft 82 is made of a stainless steel or titanium.

Figure 14A:
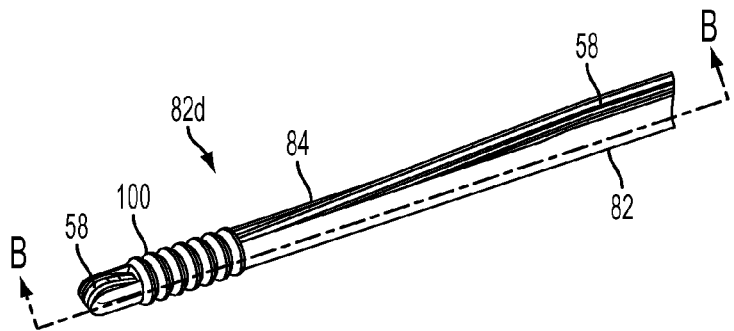
FIG. 14A is a perspective view of the distal end of the shaft of FIG. 13 coupled to an anchor having a suture filament disposed therein.
Figure 14B:
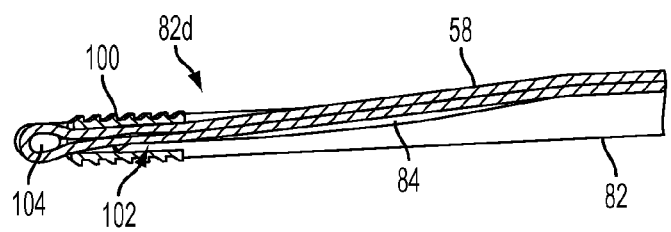
FIG. 14B is a cross-sectional view of the shaft, anchor, and suture filament of FIG. 14A taken along the line B-B.

One skilled in the art will appreciate that a variety of suture anchor types can be used in conjunction with the systems provided herein. For example, in some embodiments, such as those illustrated in FIGS. 14A and 14B, the anchor 100 can be a Gryphon™ anchor that is commercially available from DePuy Mitek, LLC. The anchor 100 can include one or more mating features, such as threads, to allow the anchor to be fixedly disposed in bone, a bore 102 formed in a proximal end and extending substantially therethrough, and a distal engagement feature 104 disposed at a distal end for receiving a suture filament 50. As shown, the limbs 54, 55, which are disposed in the sleeve 58, can extend distally down the shaft 82 of the tool 80, into the groove 84, into and through the bore 102 of the anchor 100, around the filament engagement feature 104, back through the bore 102, back into the groove 84 and out of the anchor 100, and finally proximally up the shaft 82 of the tool 80, toward the handle 90. As discussed above, limbs 54, 55 extending from the card 10' can be encapsulated in the sleeve 58' prior to entering the anchor 100 at least to assist with suture filament management.

Figure 15:
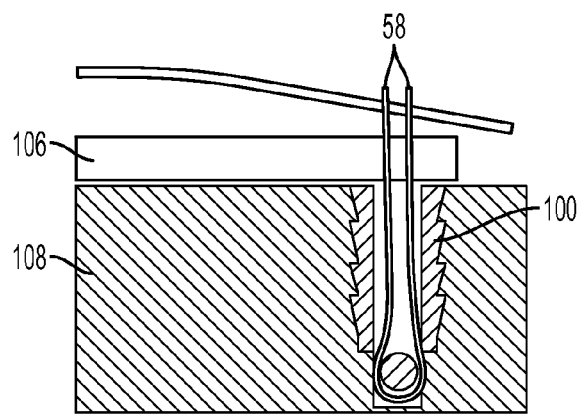
FIG. 15 is a schematic view of the anchor and suture filament of FIG. 14A implanted in bone, with the suture filament passing through soft tissue.

In one exemplary embodiment, illustrated in FIG. 15, the anchor 100, and the suture filament limbs 54, 55 disposed in the sleeve 58 attached thereto, are inserted into bone 108 and the filament limbs 54, 55 extend from the anchor 100 and through tissue 106 to be drawn to the bone 108 as described in greater detail below.

Figure 16A:
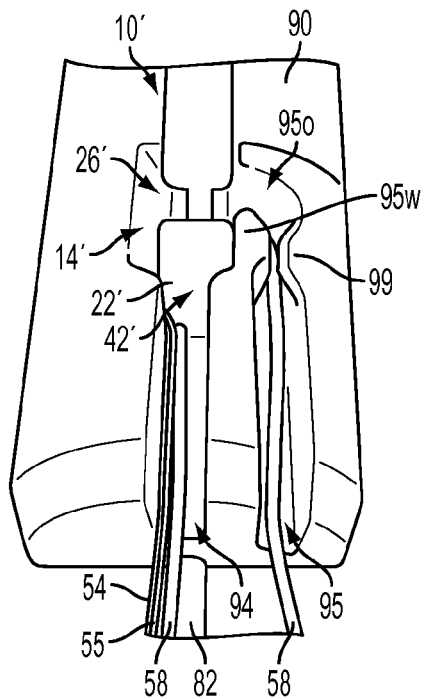
FIGS. 16A-16D are sequential views illustrating one exemplary embodiment for removing the suture management card of FIG. 5 from the handle of FIG. 2.

After the anchor 100 is inserted to the surgical site, the suture management card 10, 10' can be removed from the handle 90 and the inserter tool 80 removed from the surgical site. The configuration of the handle 90, suture management card 10', and suture filament 50 is illustrated in FIG. 16A. As shown, the card 10' is disposed in the handle 90, exposed filament limbs 54, 55 and portions of the limbs 54, 55 encapsulated by the sleeve 58 are disposed in the first suture-receiving slot 94, and the sleeve 58 is disposed in second suture-receiving slot 95. More particularly, the limbs 54, 55 extend out of the card 10' by passing through the slot 42' formed in the second surface 22' of the second end 14', through the receiving slot 94, and toward the anchor 100, with the sleeve 58 encapsulating the limbs 54, 55 at some point between the handle 90 and the anchor 100. The sleeve 58 is coupled to the anchor 100, and then extends back toward the handle 90. As shown, the sleeve 58 enters the receiving slot 94, passes through the slot 42' and into the opening 26' of the card 10', and then extends through an opening 95o disposed between the receiving slot 94 and the second suture-receiving slot 95.

Figure 16B:
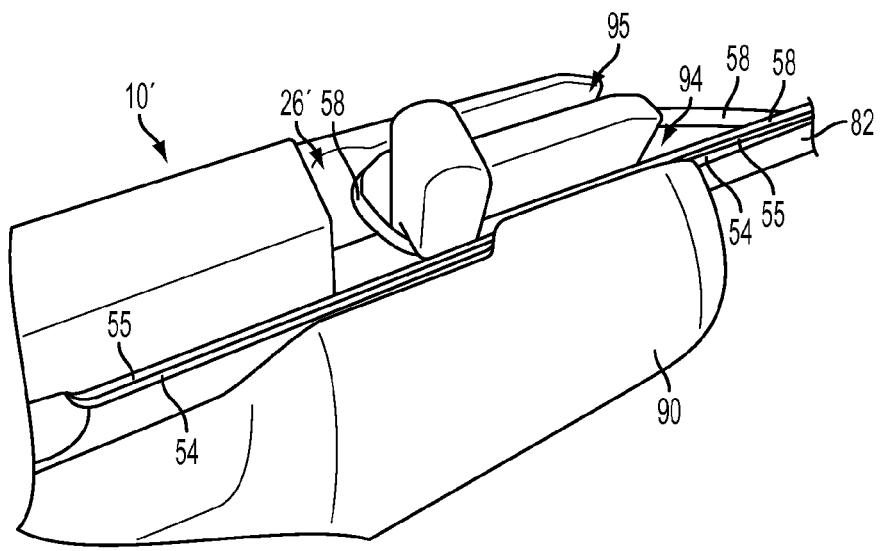
Figure 16C:
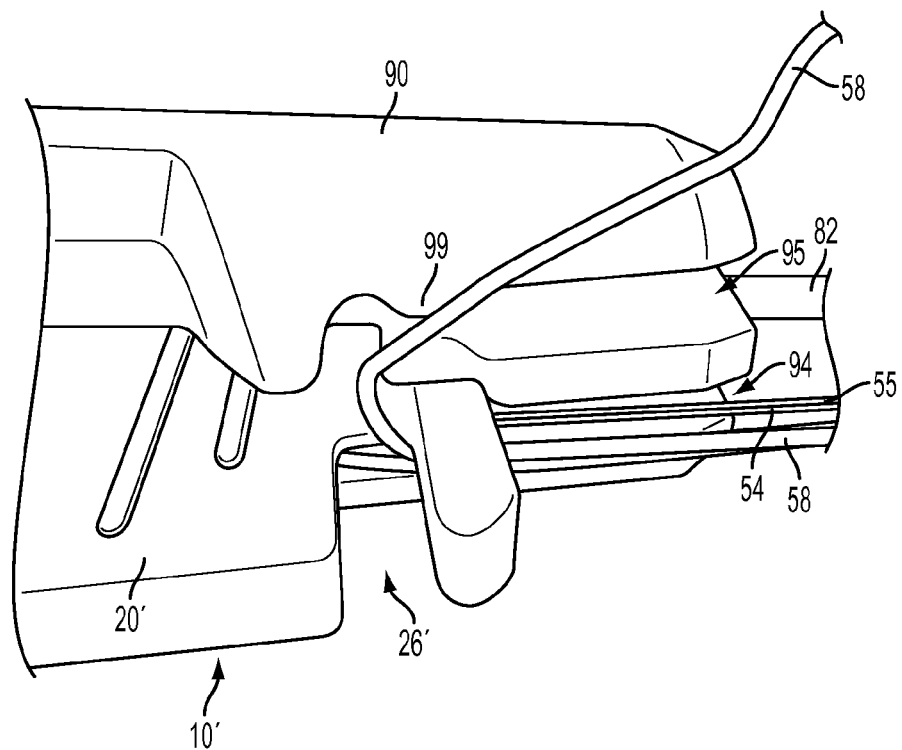
Figure 16D:
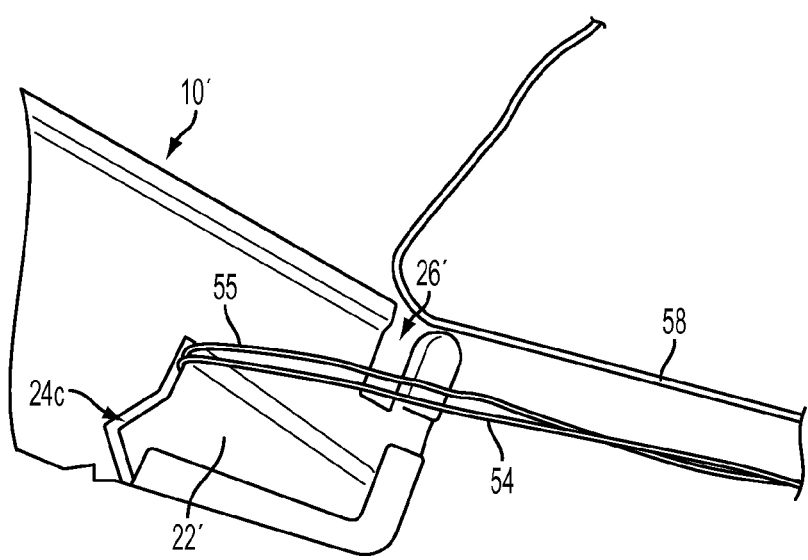

As shown in FIGS. 16B and 16C, the surgeon can lift the card 10' out of the handle 90, thereby pulling the sleeve 58 disposed in the handle 90, out of the handle 90. The open-ended slot 26' picks up the distal portion of the sleeve 58 and applies enough tension to the portion of the sleeve 58 disposed in the pinch point 99 to disengage the sleeve 58 from the pinch point 99. The design of pinch point 99 is such that it helps strip the sleeve 58 out of the slot 95 as the card 10' is removed from the handle 90. Because the slot 26' has an open end, the distal portion of the sleeve 58 can fall away from the card 10'. As shown in FIG. 16D, with the card 10' fully removed from the handle 90, the free limbs 54, 55 disposed in the sleeve 58 fall out of the open-ended slot 26' and the free limbs 54, 55 extending from the third slot 24c' are also readily identifiable by the surgeon. The repair can continue with the sleeve remaining disposed around the free limbs 54, 55, or alternatively it can be removed and the four free limbs 54, 55 can be used to complete the repair.

FIGS. 17A-17I illustrate the next steps to perform after the anchor has been implanted and the suture management card has been removed from the inserter tool. While these figures refer to the first suture management card 10 to demonstrate the steps, these steps are equally applicable to the second suture management card 10'.

As shown in FIG. 17A, the distal portion of the filament limbs 54, 55, which are disposed in the sleeve 58, can be passed through the opening defined by the collapsible loop 52. The sleeve 58 is then folded over the loop 52 so that it can be used to apply a force to the loop 52 in an approximate direction D, as shown in FIG. 17B. Once the amount of force applied by the sleeve 58 exceeds the ejection threshold tension, the loop 52 can stretch and eventually eject from the card 10, as illustrated in FIG. 17C, while the limbs 54, 55 extending from the knot 56 can remain in the slots 24, resisting the tension force. As shown in FIG. 17D, the application of force to the distal portion of the sleeve 58 in the approximate direction D in an amount that exceeds the collapsing threshold tension after the loop is ejected from the card 10 can draw the sliding knot 56 toward the distal portions of the sleeve 58, i.e., cinching the loop. Again the limbs 54, 55 extending from the knot 56 can remain substantially in the same position with respect to the slots 24. It is the resistance created by the limbs 54, 55 disposed in the slots 24 that the knot 26 draws towards the distal portion of the sleeve 58. Eventually, the force is such that the knot 56 slides all the way to the location where the force is being applied by the sleeve 58, as shown in FIG. 17E.

Figure 17F:
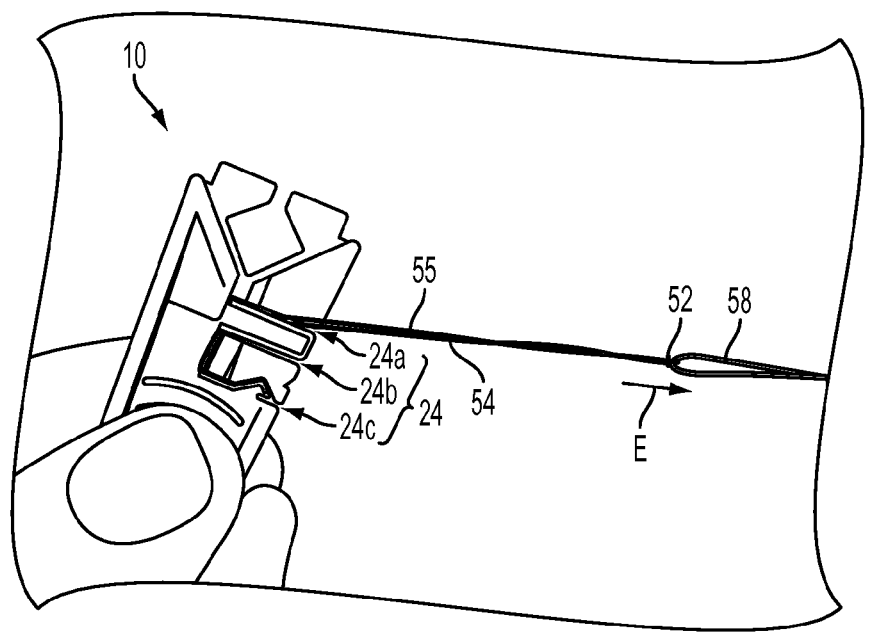
Figure 17G:
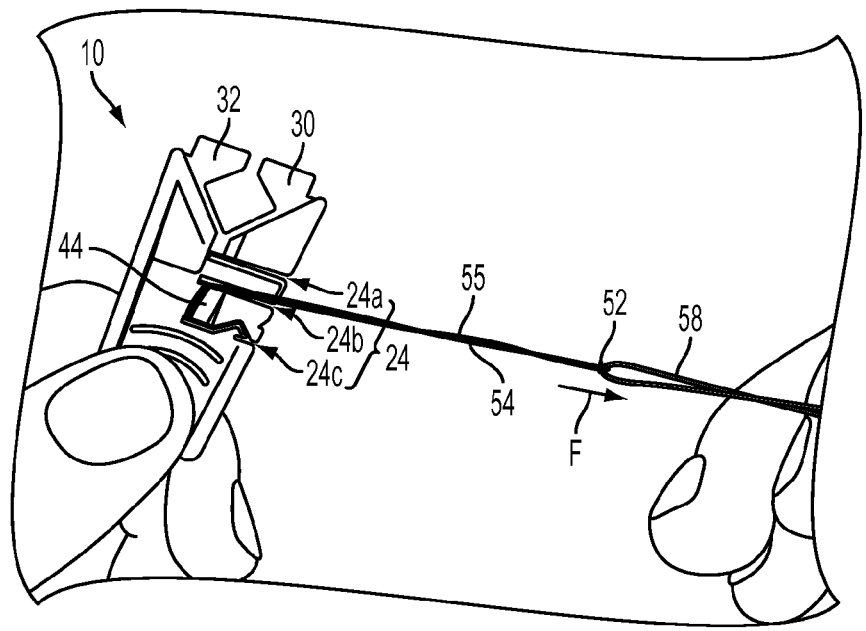
Figure 17H:
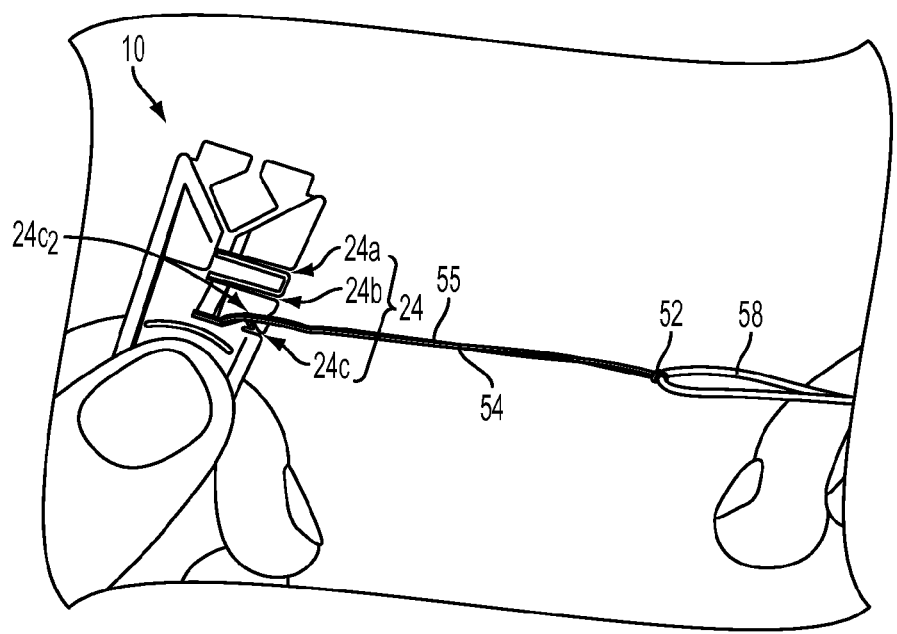
Figure 17I:
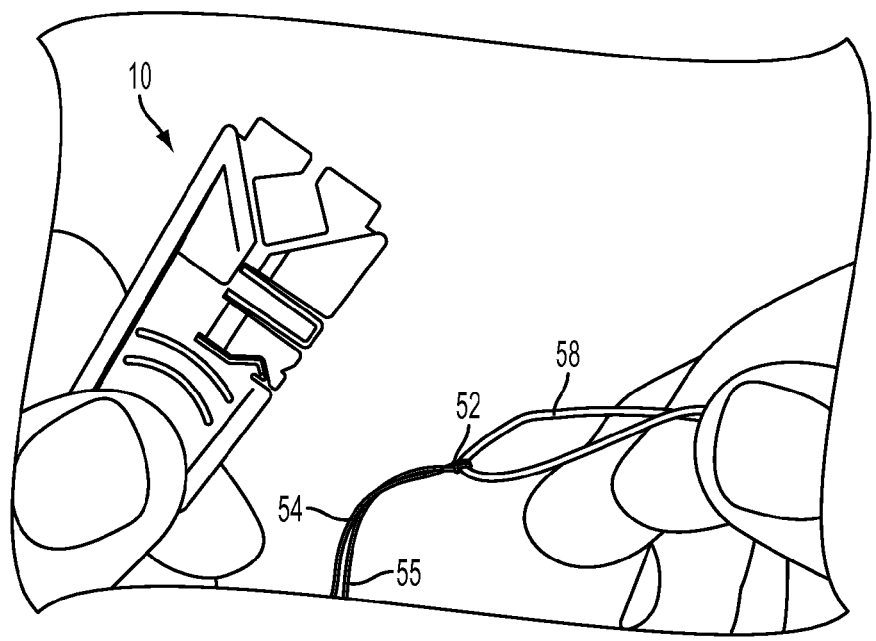

Once the knot 56 is adjacent to the sleeve 58 and the loop 52 is thus fully collapsed, tension can be applied by the sleeve 58 in a different direction to help offload the remaining portions of the filament 50 from the card 10. As shown in FIG. 17F, a force can be applied in an approximate direction E to dislodge the filament limbs 54, 55 from the first slot 24a. Likewise, as shown in FIG. 17G, a force can be applied in an approximate direction F to dislodge the filament limbs 54, 55 from the second slot 24b. Because in the illustrated embodiment the raised section 44 is ramped, and the loop 52 is no longer mounted on the prongs 30, 32, the raised section 44 does not make offloading difficult like it did before the loop 52 was ejected off the card 10. Further, as shown in FIG. 17H, forces can be applied to dislodge the filament limbs 54, 55 from the third slot 24c. Because the third slot 24c includes the V-shaped second portion 24c₂, forces will typically need to be applied in more than one direction to work the suture limbs 54, 55 up and over the vertex of the V-shaped portion and then out of the remaining portion of the third slot 24c. Once the suture filament 50 is fully removed from the suture management card 10, as shown in FIG. 17I, the card 10 can be discarded or reloaded with another suture for use, while the suture filament 50 can be used to complete the soft tissue repair.

Figure 18A:
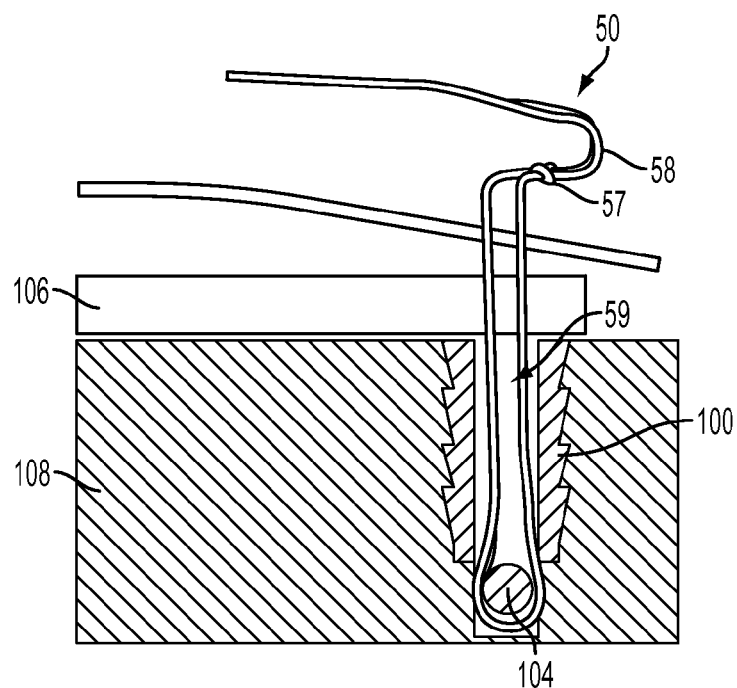
FIGS. 18A-18D are sequential views illustrating one exemplary embodiment for using the suture filament of FIG. 15 to secure soft tissue to bone.

As shown in FIG. 18A, with the suture filament 50 disassociated from the suture management card, the anchor 100 and filament 50 combination can be used to complete the soft tissue repair. A circled loop 57 is formed at the location of where the sliding knot 56 is cinched against the distal portion of the sleeve 58. As shown, the cinched loop 57 defines a new loop 59 that extends distally from one side of the cinched loop 57, around the distal engagement feature 104 of the anchor 100. Extending proximally from the other side of the cinched loop 57 are the terminal ends of the filament limbs 54, 55, which as shown can still be disposed in the sleeve 58.

Figure 18B:
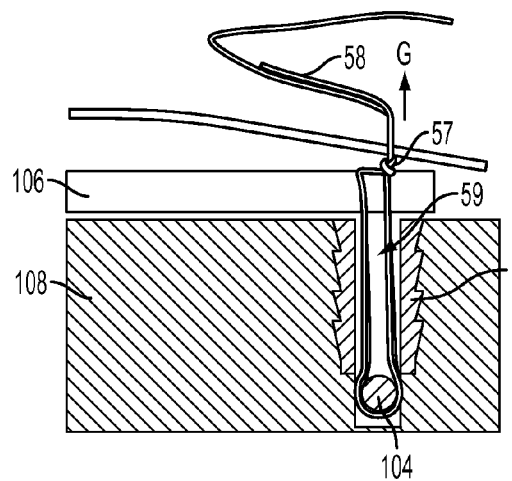
Figure 18C:
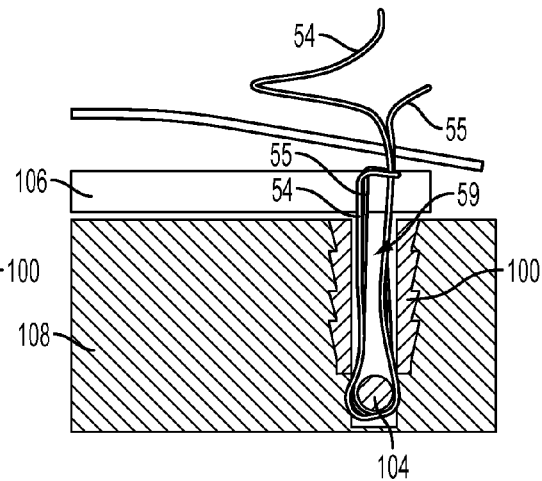
Figure 18D:
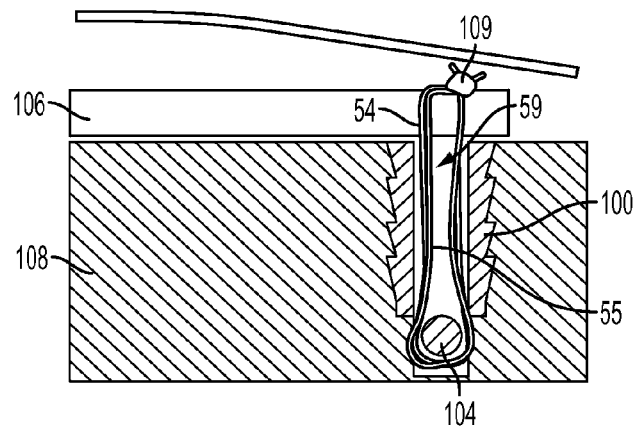

As shown in FIG. 18B, tension can be applied to the sleeve 58 by pulling in an approximate direction G, thereby causing the cinched loop 57 to slide distally toward the tendon 106 in a zip-line like manner until the cinched loop 57 is adjacent to the tendon 106. As shown in FIG. 18C, the sleeve 58 can be removed, thereby exposing the first and second limbs 54, 55. The limbs 54, 55 can then be cinched or otherwise tied together to assist in securing a location of the cinched loop 57, and thus the tendon 106, with respect to the bone 108, as illustrated in FIG. 18D. In the illustrated embodiment, a half-hitch 109 is formed by the surgeon using the first and second limbs 54, 55. A second half-hitch can be formed to lock the location of the first half-hitch 109, and thus the loop 59 and tendon 106.

Although in the illustrated embodiment the construct is passed through two portions of tendon 106, alternatively the construct can be passed through only one portion of tendon or tissue while the second portion of the construct can be free of the tendon or tissue. Such an embodiment can be used, for example, during a labral repair. Either of the two ends can be the end that is not passed through the tendon or tissue, although in some exemplary embodiments the end not with the knot and extending from the card is not the end passed through the tendon or tissue. Further, in some embodiments, rather than passing through tissue, a repair construct can be coupled to tissue using other techniques, such as, for example, by wrapping the construct around the tissue.

One skilled in the art will appreciate further features and advantages of the invention based on the above-described embodiments. Accordingly, the invention is not to be limited by what has been particularly shown and described, except as indicated by the appended claims. Further, although the constructs and methods provided for herein are generally directed to surgical techniques, at least some of the constructs and methods can be used in applications outside of the surgical field. All publications and references cited herein are expressly incorporated herein by reference in their entirety.

What is claimed is:
1. A surgical suture management device, comprising:
a suture loop management card configured to hold open a collapsible loop of a suture, the suture management card having:
a first end and a second end defining a length of the card;
first and second sidewalls extending between the first and second ends and defining a width of the card;
first, and second surfaces defining a thickness of the card;
a first slot, a second slot, and a third slot, each formed in the card and disposed between the first and second ends, each slot extending from the first sidewall toward the second sidewall with an end of each slot that is at the first sidewall being disposed a distance away from the first and second ends, and each slot being configured to receive a portion of one or more limbs of the suture;
a raised surface formed on the first surface of the card between the second and third slots; and
first and second prongs extending longitudinally away from the first end, beyond the defined length of the card by at least one of the first and second sidewalls, the first and second prongs being configured to hold open the collapsible loop,
wherein the first and second slots are substantially parallel to one another and substantially perpendicular to a longitudinal axis extending the length of the card, the first and second slots terminating at a location that is substantially centered between the first and second sidewalls, the second slot being disposed closer to the second end than is the first slot, and
wherein the third slot is disposed closer to the second end than is the second slot and has a first portion extending from the first sidewall, a second portion adjacent to and in communication with the first portion, a third portion adjacent to and in communication with the second portion, with the second portion being substantially V-shaped with a vertex facing the first end and the third portion being substantially parallel with the first and second slots.

2. The device of claim 1, further comprising an opening formed in the second end of the card and configured to receive a distal portion of one or more limbs of the suture.

3. The device of claim 1, wherein the first and second prongs are configured to hold open the collapsible loop of the suture until a force applied to the loop is greater than a threshold tension.

4. The device of claim 1, wherein the first end further comprises an opposed pair of seating grooves formed in the first surface of the card, each seating groove extending diagonally from the first end and toward the second end, the seating grooves meeting at a vertex substantially centered between the first and second sidewalls and in communication with a longitudinal seating groove formed in the first surface of the card, the seating grooves being configured to receive a length of the collapsible loop therein and the longitudinal seating groove being configured to receive a sliding knot of the collapsible loop.

5. The device of claim 1, further comprising a catch slot formed in the card, the catch slot extending from the first portion of the third slot, toward the second sidewall, and inward of a base of the V-shaped second portion.

6. The device of claim 1, further comprising a notch formed in the first sidewall between the second and third slots.

7. The device of claim 1, further comprising a protrusion formed on the second surface of the card and configured to engage a complementary retention feature of an insertion tool to secure an attachment of the device to the insertion tool.

8. The device of claim 1, further comprising a suture having a sliding knot formed therein, the sliding knot having on one side thereof a collapsible loop and on the other side thereof first and second free limbs,
wherein the collapsible loop is held open by the first end of the suture management card, and
wherein the first and second free limbs are disposed in the first, second, and third slots.

9. A suture management card, comprising:
a first end and a second end defining a length of the card, the first end being configured to hold open a collapsible loop of a suture;
first and second sidewalls extending between the first and second ends and defining a width of the card;
first and second surfaces defining a thickness of the card; and
a slot formed in the card and disposed between the first and second ends, the slot having a first portion that extends from the first sidewall toward the second sidewall, a second portion adjacent to and in communication with the first portion, the second portion being substantially V-shaped with a vertex facing the first end, and a third portion adjacent to and in communication with the second portion, the third portion being substantially parallel to at least one of the first and second ends,
wherein the first portion of the slot extends toward the second end a distance beyond a start of the second portion to form a catch slot.

10. The suture management card of claim 9, further comprising:
a second slot and a third slot both formed in the card, both extending from the first sidewall toward the second sidewall, both disposed between the first and second ends with the second slot being closer to the first end that each of the first and third slots and the third slot being closer to the first end than the first slot, both the second and third slots being substantially parallel to the third portion of the first slot, and both the second and third slots being configured to receive a portion of one or more limbs of the suture.

11. The suture loop management card of claim 10, wherein the second and third slots are substantially parallel to one another and substantially perpendicular to a longitudinal axis extending the length of the card, the second and third slots terminating at a location that is substantially centered between the first and second sidewalls.

12. The suture loop management card of claim 9, wherein the first portion of the slot is substantially collinear with the third portion of the slot.

13. A suture management card, comprising:
a first end and a second end defining a length of the card along a longitudinal axis of the card, the first end being configured to hold open a collapsible loop of a suture;
first and second sidewalls extending between the first and second ends and defining a width of the card;
first and second surfaces defining a thickness of the card; and
a slot formed in the card, extending from the first sidewall toward the second sidewall and disposed between the first and second ends, the slot having two paths,
wherein the first path extends toward the second sidewall and is substantially perpendicular to the longitudinal axis of the card,
wherein the second path extends toward the second sidewall and forms an oblique angle with respect to the first path, and
wherein a portion of the second path forms a V-shape with a vertex facing the first end, and the second path further includes a substantially straight portion after the portion of the second path forms the V-shape, the substantially straight portion being substantially perpendicular to the longitudinal axis of the card and is substantially collinear with the first path.

14. The suture management card of claim 13, further comprising:
a second slot and a third slot both formed in the card, both extending from the first sidewall toward the second sidewall, both disposed between the first and second ends with the second slot being closer to the first end that each of the first and third slots and the third slot being closer to the first end than the first slot, both the second and third slots being substantially parallel to the first path of the first slot, and both the second and third slots being configured to receive a portion of one or more limbs of the suture.

* * * * *